(12) United States Patent
Raaz et al.

(10) Patent No.: US 12,714,503 B2
(45) Date of Patent: Aug. 25, 2026

(54) METHOD FOR DEFINING A PLACEMENT POSITION

(71) Applicant: Angiolutions GmbH, Hannover (DE)

(72) Inventors: Uwe Raaz, Leipzig (DE); Isabel Nahal Schellinger, Leipzig (DE)

(73) Assignee: Angiolutions GmbH, Hannover (DE)

( * ) Notice: Subject to any disclaimer, the term of this patent is extended or adjusted under 35 U.S.C. 154(b) by 572 days.

(21) Appl. No.: 18/230,550

(22) Filed: Aug. 4, 2023

(65) Prior Publication Data

US 2024/0041528 A1 Feb. 8, 2024

(51) Int. Cl.

*A61F 2/82* (2013.01)
*A61B 34/10* (2016.01)
*G16H 20/40* (2018.01)

(52) U.S. Cl.

CPC ............. *A61B 34/10* (2016.02); *G16H 20/40* (2018.01); *A61B 2034/107* (2016.02); *A61B 2034/108* (2016.02); *A61F 2002/823* (2013.01)

(58) Field of Classification Search

CPC .............. A61B 34/10; A61B 2034/107; A61B 2034/108; A61B 2090/3762; G16H 20/40; A61F 2002/823

See application file for complete search history.

(56) References Cited

U.S. PATENT DOCUMENTS 6,395,018 B1 * 5/2002 Castaneda ................ A61F 2/07 623/1.13
10,779,964 B2 * 9/2020 Raaz ........................ A61F 2/82
11,540,912 B1 * 1/2023 Bernshtein ................ A61F 2/07
2009/0088830 A1 4/2009 Mohamed et al.
2011/0022153 A1 * 1/2011 Schreck .................. A61F 2/856 623/1.13
2016/0310303 A1 * 10/2016 Thapliyal .................. A61F 2/90
2019/0083227 A1 * 3/2019 Barone ..................... A61F 2/07
2020/0188027 A1 6/2020 Sakuragi
2021/0137634 A1 * 5/2021 Lang ...................... A61B 5/113
2023/0063108 A1 * 3/2023 Magen ...................... A61F 2/07
2023/0346538 A1 * 11/2023 Adler .................. A61B 5/0031
2024/0188833 A1 * 6/2024 Samaneigo ........... G06T 7/0012

(Continued)

FOREIGN PATENT DOCUMENTS

WO WO-2024256392 A1 * 12/2024 ............. G16H 50/50
WO WO-2026035928 A1 * 2/2026

OTHER PUBLICATIONS

Extended European Search Report dated Jan. 3, 2023 issued in EP Patent Application No. 22188715.1.

*Primary Examiner* — Suzette J Gherbi
(74) *Attorney, Agent, or Firm* — Blank Rome LLP

(57) ABSTRACT

A planning method for defining a placement position of a stent in an abdominal aorta of a subject is described. An abdominal aortic aneurysm portion of the abdominal aorta has an aneurysm sac and an aneurysm neck, a distal end of the aneurysm neck, a lower renal aortic ostium, a first distance between a distal end of the lower renal aortic ostium and the distal end of the aneurysm neck, and a second distance between a proximal end of the lower renal aortic ostium and the distal end of the aneurysm neck are identified in image data. The first distance is compared with a minimum stent length. A stent placement position is defined based on a selected stent length such that a distal end of the stent is aligned with the distal end of the aneurysm neck.

22 Claims, 13 Drawing Sheets

(56) References Cited

U.S. PATENT DOCUMENTS

| | | | | |
|---|---|---|---|---|
| 2024/0252178 | A1* | 8/2024 | Walzman | B33Y 80/00 |
| 2024/0277342 | A1* | 8/2024 | Jimenez | A61F 2/07 |
| 2025/0079020 | A1* | 3/2025 | Forneris | A61B 34/10 |
| 2025/0312098 | A1* | 10/2025 | Pai Raikar | A61B 34/10 |
| 2026/0060659 | A1* | 3/2026 | Shaked | A61B 8/54 |

* cited by examiner 220, 205
F1, COF1
F1, COF1
222, 205a
20
DN 220, 205
F2, COF2
F2, COF2
222, 205a
Dmax Stentexpansion Ringsegment - Radialkraft
S1
S2
COF1
P1
S3
K
COF2
P2
S4
F1
F2
E
D*
DW
Ringsegment - Durchmesser

F
S1
230
COF₁
S3
K
S2
232
234
COF₂
236
S4
D₁
D₂
238

20
220
222
220
203a
240
242
b1
b2
L1
L2
202
202a 204
207

METHOD FOR DEFINING A PLACEMENT POSITION

CROSS-REFERENCE TO RELATED APPLICATION

This application claims foreign priority to EP Application No. 22188715.1, filed Aug. 4, 2022, the disclosure of which is hereby incorporated by reference herein in its entirety.

FIELD OF THE INVENTION

The invention relates to a planning method for defining a placement position of a stent in an abdominal aorta of a subject, in particular a human patient outside the human body. The invention further relates to a use of a self-expandable stent in a method of the aforementioned type. The method is a pre-invasive method.

BACKGROUND

Abdominal aortic aneurysm (AAA) is a pathological focal dilation of the abdominal aorta that is progressive in nature and carries a high mortality rate in case of rupture.

Abdominal aortic aneurysm (AAA) formation is at least in part due to active, dynamic tissue remodelling and mechanical wall stress is a critical driver of this process. Laplace's law is commonly used to explain this phenomenon, dictating that an increasing diameter of a pressurized vessel (i.e., that AAA sac) directly translates into increased wall stress.

Additionally, from U.S. Pat. No. 10,779,964 B2 and the scientific publication "Segmental Aortic Stiffening Contributes to Experimental Abdominal Aortic Aneurysm Development" published in "Circulation" 2015; 131:1783-1795 of the same inventors as named herein, it is known that segmental aortic stiffening as an early pathomechanism generates aortic wall stress and triggers aneurysmal growth—independently of the AAA geometry. The reason is that an aneurysmal portion of a vessel, as e.g. the aorta, has a higher wall stiffness than the other adjacent parts on the vessel (e.g., the AAA neck), which introduces wall stress in the transition between the siff aneurysm and the healthy and more compliant portion of the vessel, which in turn leads to the growth of the aneurysm.

For treating an abdominal aortic aneurysm in U.S. Pat. No. 10,779,964 B2, a method has been proposed, which comprises treating, in a targeted manner, an aortic segment axially adjacent the abdominal aortic aneurysm in the subject, whereby a mechanical stiffness of the aortic segment is increased. The idea of the invention disclosed in U.S. Pat. No. 10,779,964 B2 is to increase the mechanical stiffness of an aortic segment adjacent to the abdominal aortic aneurysm in the subject. Increasing mechanical stiffness of the aortic segment in one embodiment may comprise deploying an intravascular stent that stiffens the aortic segment. In that the segment adjacent to the aortic aneurysm is stiffened, a stiffness gradient between the aneurysm itself (AAA sack) and the healthy portion of the vessel is reduced which in turn reduces growth of the aneurysm itself. According to this disclosure, the stent may be an expandable stent that is configured to expand into contact with the inner wall of the aorta, thereby providing support and mechanical stiffness to the length of the aorta with which the stent is in contact.

SUMMARY OF THE INVENTION

While the general idea of stiffening a portion of the respective vessel adjacent to the aneurysm works very well and has shown outstanding results, the inventors have found that it is important to plan the placement of the stent and the size of the stent properly in order to achieve best results. In particular, it is important before the actual intervention to properly define a placement position of the stent in the abdominal aorta. For instance, the identification and axial localization of the distal end of the AAA neck along the aorta relative to other (anatomical) landmarks is of paramount importance to plan and guide the later stent implantation.

Therefore, it is an object of the invention to provide a pre-invasive method for defining a placement position of a stent in an abdominal aorta of the human patient outside the human body. A further object of the invention is to provide a stent for use in the above method and an imaging apparatus for use in planning the placement of the stent.

In a first aspect of the invention, the object is solved by a planning method according to claim 1. The method comprises the steps: providing image data representing at least a portion of the abdominal aorta of the subject; identifying in said image data: an abdominal aortic aneurysm (AAA) portion of the abdominal aorta having an aneurysm sac and an aneurysm neck, a distal end of the aneurysm neck, a lower renal artery, and a first distance between a distal end of the lower renal aortic ostium and the distal end of the aneurysm neck, and a second distance between a proximal end of the lower renal aortic ostium and the distal end of the aneurysm neck. The planning method further includes the steps: comparing the first distance with a minimum stent length and in case the first distance is larger than the minimum stent length, selecting a stent length smaller than the first distance or larger than the second distance, and in case the first distance is smaller than the minimum stent length, selecting a stent length larger than the second distance; and defining a stent placement position in accordance with the selected stent length with a distal stent end aligned with the distal end of the aneurysm neck.

The subject preferentially is a human patient although other subjects may be envisaged. The terms "proximal" and "distal" in this instance always refer to the position relative to the heart of the subject. Thus, the term "distal" describes elements which are farther away from the heart, while the term "proximal" defines elements which are closer to the heart.

The invention is based on the idea that a proper placement of the stent is crucial to stop further aneurysmal growth, in particular as the stent will remain in the body for a long time. Typical patients of small abdominal aortic aneurysms are male persons aged 65+. The inventors have found that on the one hand it is important that the stent is placed directly adjacent the aneurysm and thus, that a distal stent end, i.e., the end of the stent, which is farther away from the heart, is aligned with the distal end of the aneurysm neck, i.e., the proximal end of the aneurysm sac. The closer the stent is placed to the aneurysm sac, the better aneurysmal growth can be further prevented. Furthermore, the stent should have a length which is sufficient for stiffening a substantial portion of the arterial segment adjacent to the aneurysm sac, so that aneurysmal growth is effectively prevented. The proximal end of the stent according to the placements of the present invention however must not be positioned at a lower renal aortic ostium but rather be positioned either distal of the lower renal aortic ostium, or proximal thereof. The lower renal artery typically is the one leading to the right kidney and thus can be named "right renal artery". The inventors have found that it is generally not problematic when the stent fully covers the lower renal aortic ostium, since the stent does not obstruct the lumen in such a way which would adversely affect an otherwise healthy subject. Rather, it is more important to have a sufficiently long stent for preventing aneurysmal growth. The term "aortic ostium" defines the orifice of the artery transition from the abdominal aorta to the respective side vessels.

The image data used is image data which is obtained prior to an intervention and preferably prior to carrying out the claimed method. The image data may include computed tomographical image data, X-ray image data, magnetic resonance image data, and/or ultrasound image data. The image data preferentially is provided by a representation providing unit.

The representation providing unit may be a storing unit, in which the image data of the subject is stored already and from which the stored image data can be retrieved for providing the same. The representation providing unit can also be a receiving unit for receiving the image data of the subject and for providing the received image data. Moreover, the representation providing unit can be adapted to generate the image data of the subject. For instance, the representation providing unit can be an imaging modality for generating image data of the subject, wherein the generated image data may be regarded as being the image data. The imaging modality can be, for instance, a magnetic resonance imaging modality, a computed tomography imaging modality, a nuclear imaging modality like a positron emission tomography or a single photon emission tomography imaging modality, an ultrasound imaging modality, et cetera.

The steps of identifying the different anatomical elements may be completely or partially automatized, in particular using image recognition methods. Preferably, the defined stent placement position is identified in the image data, and/or additional image data is generated, which includes data representing the defined stent placement position, and is stored to a storage. The identification of the different anatomical elements preferentially is carried out by a recognition unit which preferably is adapted to identify in the image data the different anatomical elements and preferably marks or attributes them in the image data.

According to a preferred embodiment, a proximal stent end is positioned between the distal neck end and the distal end of the lower renal aortic ostium or proximal of the proximal end of the lower renal aortic ostium in the stent placement position. Thus, the proximal stent end is not positioned in the region of the lower renal aortic ostium and therefore is prevented from kinking into the lower renal aortic ostium, which could adversely affect placement position and vessel stability.

In a further preferred embodiment, the planning method includes the steps: identifying in said image data a higher renal artery, a third distance between a distal end of a higher renal aortic ostium and the distal end of the aneurysm neck, and a fourth distance between a proximal end of the higher renal aortic ostium and the distal end of the aneurysm neck. Again, these steps can be carried out by a recognition unit which is preferentially adapted to carry out these steps. The planning method further preferably comprises the steps: comparing the third distance with the minimum stent length and in case the third distance is larger than the minimum stent length, selecting a stent length smaller than the third distance or larger than the fourth distance, and in case the third distance is smaller than the minimum stent length, selecting a stent length larger than the fourth distance. The higher renal artery typically is the left renal artery, leading to the left kidney of the human body. Again, as already described with respect to the lower renal artery, it is typically not problematic if the stent extends over the higher renal aortic ostium, as the stent typically does not affect the flow in the higher renal artery adversely.

Rather, the stent extending above the fourth distance, that is even more proximal to the heart, can be safely anchored and provide stiffening to the vessel for reliably preventing aneurysmal growth. Preferably, the steps of identifying the third and fourth distance are completely or partially carried out automatic, preferably by the recognition unit. In particular, image recognition methods can be used for identifying the third and fourth distance in the image data.

In a further preferred embodiment, the planning method comprises the steps: identifying in said image data a superior mesenteric artery and a fifth distance between a distal end of the superior mesenteric aortic ostium and the distal end of the aneurysm neck, and a sixth distance between a proximal end of the superior mesenteric aortic ostium. Preferably, these steps are carried out by the recognition unit. The planning method preferably further comprises: comparing the fifth distance with the minimum stent length and in case the fifth distance is larger than the minimum stent length, selecting a stent length smaller than the fifth distance. It is preferred that the proximal stent end is positioned distal from the distal end of the superior mesenteric aortic ostium, so that the stent does not cover the superior mesenteric aortic ostium.

In case the fifth distance is smaller than the minimum stent length, a decision might be made in which no stent is implanted and a different procedure for therapy of the aneurysm might be chosen. However, typically, the fifth distance is large enough for accommodating a stent sufficiently long for reliably preventing further aneurysmal growth.

According to a further preferred embodiment, the planning method comprises the steps: identifying in said image data a neck diameter at the distal end of the aneurysm neck and selecting a nominal stent diameter based on the neck diameter. The nominal stent diameter is not selected based on the size of the aneurysmal sac but rather only based on the neck diameter. Preferentially, the nominal stent diameter is at least 1.05, preferably 1.1 times the neck diameter and/or at most 1.2, preferably 1.25 times the neck diameter. That is, the nominal stent diameter is slightly larger than the neck diameter. By means of this setting, two important aspects are achieved. On the one hand, the stent is securely anchored to the inner wall of the vessel. On the other hand, by setting the stent diameter at least 5% and preferably between 10% and 20% larger than the neck diameter, the vessel can be slightly stretched by means of the stent which in turn increases stiffening of the vessel wall which in turn is beneficial for preventing further aneurysmal growth. Moreover, the effect of remodelling of the vessel has been described above, and the stent will be remaining in the vessel for a rather long time. Thus, the likelihood that remodelling of the vessel takes place is rather high, and in that the nominal stent diameter is chosen to be larger than the neck diameter, a remodelling of the vessel can be taken into account while still the stent is able to provide a chronic outward force after the vessel has experienced remodelling.

In a further preferred embodiment, the nominal stent diameter can also be selected based on the aorta diameter. For achieving this, the planning method may include the step of identifying in said image data an aorta diameter preferably at a position proximal of said proximal end of the lower renal aortic ostium and selecting the nominal stent diameter based on this aorta diameter. It is further preferred that the nominal stent diameter is selected on both, the neck diameter and the aorta diameter. It is further preferred that a stent is selected having a nominal stent diameter gradient, i.e., a stent with different diameters and/or a stiffness gradient, i.e., a stent with different stiffness at a position placed in the neck and at a position placed in the aorta close to the proximal end of the lower renal aortic ostium. This allows to induce a stiffness gradient in the vessel wall. The inventors have found that it is beneficial that a stiffness of the vessel wall is higher closer to the aneurysm sac and that this wall stiffness beneficially is gradually reduced.

Preferably, the abdominal aortic aneurysm (AAA) has a diameter of 5.5 cm or less. Abdominal aortic aneurysms with such a diameter are considered to be small abdominal aortic aneurysms and placement of a stent according to the planning method disclosed herein is well suited for those small abdominal aortic aneurysms in order to stop the further growth. In general, abdominal aortic aneurysm carries a high mortality in case of rupture. Current therapies are limited to open surgical or interventional (stent-)graft-based exclusion of the aneurysmal sac from the circulation in order to prevent rupture. Above cited U.S. Pat. No. 10,779,964 B2 provides a method for treating also small abdominal aortic aneurysms. Therefore, it is particularly preferred that the planning method disclosed herein is used in cases where the abdominal aortic aneurysm has a diameter of 5.5 cm or smaller.

In the planning method disclosed herein, it is further preferred that the minimum stent length is 20 mm, preferably 25 mm, preferably 30 mm, preferably 35 mm, further preferred 40 mm.

In a further preferred embodiment, the planning method comprises the steps: generating pre-surgical image data based on said image data representing at least a portion of the abdominal aorta of the patient and including stent placement data representing said stent placement position. Preferably, said pre-surgical image data includes at least one patient specific landmark, and the stent placement data is defined relative to said patient specific landmark. Alternatively, the stent placement data can also be defined relative to a set coordinate system which may be registered to the image data and used in a surgical navigation system. The patient specific landmark preferably is a bone, in particular a portion of a spine represented in the image data. The stent placement data may include a graphical representation of the defined stent placement position, which indicates the proximal stent end and/or the distal stent end, and/or coordinate data relating to a coordinate system and/or the landmark of the patient, and/or a delivery position for a delivery system of the stent. Moreover, the stent placement data may include vector data. The stent placement data or a visualization of the stent placement data may be viewed on a graphical user interface, in particular a display, before and/or during an intervention. The stent placement data or a visualization of the stent placement data may also be only used pre-invasive in planning the intervention.

In a further preferred embodiment, the stent has a proximal section and a distal section, said distal section being positioned adjacent to the aneurysm sac and said proximal section being positioned away from said aneurysm sac. Said distal section preferably generates a higher radial force (in particular chronic outward force and/or radial resistive force) than said proximal section. A higher radial force provides a higher stiffening of the vessel wall and thus the ability of an improved adjustment of the stiffness of the vessel portion adjacent to the aneurysm, i.e., in particular the aneurysm neck, and the aneurysm itself. Preferably, the chronic outward force at the proximal end of the stent is close to zero but preferably not zero. The proximal section and the distal section might each have a distinct radial force, or the radial force may gradually decrease from the distal end to the proximal end. Moreover, it is preferred that the stent does not only have two sections, the proximal section and the distal section, but at least one preferable multiple intermediate section such that section by section the radial force can decrease in a pseudo-continuous manner.

While stent implantation in the AAA neck segment is beneficial in in reducing the distal stiffness gradient towards the AAA sack thereby minimizing mechanical stress driving AAA growth, it may, however, de novo generates a stiffness gradient at the proximal end of the stent. This might—at least theoretically—induce adverse mechanical forces potentially leading to proximal aneurysm growth. To minimize this risk, the stent design may incorporate features to gradually reduce its wall stiffening effects from its distal to proximal end.

In a preferred embodiment, the distal section of the stent has a higher radial stiffness than the proximal section. A higher stiffness of the stent section can be used to generate a higher radial force. In this case, also a stiffness gradient, which might be continuous or discrete as described above, is preferably implemented in the stent.

In a further preferred embodiment, the ratio of the radial force of the distal section to the chronical radial outward force of the proximal section is at least 1.1 and/or at most 10.0. Preferably, the ratio is in a range of 1.1 to 9.0, preferably 1.1 to 6.0, preferably 1.5 to 6.0, preferably 2.0 to 6.0, preferably 2.5 to 6.0, preferably 3.0 to 6.0, preferably 3.5 to 6.0, preferably 4.0 to 6.0, preferably 1.1 to 5.5, preferably 1.5 to 5.5, preferably 2.0 to 5.5, preferably 2.5 to 5.5, preferably 3.0 to 5.5, preferably 3.5 to 5.5, preferably 4.0 to 5.5.

In a further preferred embodiment, the stent is an uncovered stent which is preferably self-expanding. The stent is at least partially uncovered, in particular the stent is at least uncovered in section where the lower or the upper renal artery branch from the aorta, to allow blood flow from the aorta to the lower and higher renal arteries.

Preferably, at least the distal segment of the stent has a radial force/chronic outward force (COF) of 1 N/mm or more, 1.5 N/mm or more, 2.0 N/mm or more, or 2.5 N/mm or more. Chronic outward force in this range is beneficial usable for stiffening the vessel wall to prevent further aneurysmal growth. The total amount of the force is dependent on the axial length of the stent.

In a further preferred embodiment of the method, the stent has a crimped state with a minimum diameter and an expanded state with a nominal diameter, wherein the stent has a first expansion characteristic for a first diameter range, smaller than the nominal diameter, and a second expansion characteristic for the second diameter range, larger than the nominal diameter.

Preferentially it is provided that the stent has a first diameter radial stiffness in the first diameter range, and a second diameter radial stiffness in the second diameter range, wherein the first diameter radial stiffness is higher than the second diameter radial stiffness. More generally, the stent has a first expansion characteristic in the first diameter range and a second expansion characteristic in the second diameter range. The stent initially expands at a high predefinable first radial force (F1) or to the level of the predefinable first radial force (F1) until a specific nominal diameter is reached. Beyond the nominal diameter, the stent allows further expansion until a specific maximum diameter is reached. The difference between the nominal and maximum diameters corresponds to the "expansion reserve" of the stent. If the stent enters from its nominal diameter into the expansion reserve, its radial force decreases abruptly (in steps) to a considerably lower radial force level of a predefinable second radial force (F2), which acts until the maximum diameter is reached.

Here, it is preferably provided that the first expansion characteristic causes an expansion with a first chronic outward force (COF1) and the second expansion characteristic causes an expansion with a second chronic outward force (COF2) that is lower than the first permanent outward force (COF1).

In this way, a stepped radial force profile can be achieved, which allows the stent to expand up to the nominal diameter and the corresponding vessel to expand to the nominal diameter, but beyond the nominal diameter only allows the stent to widen along with it, applying only a very small radial force or chronic outward force in this region. The radial force or chronic outward force (COF2) in the second diameter range, i.e., in the range beyond the nominal diameter to the maximum diameter, is preferably chosen to be as small as possible and to follow the vessel wall during adaptive remodeling. The radial force or the second permanent outward force (COF2) in the second diameter range should preferably be selected so that active further expansion of the vessel does not occur, but the radial force is merely selected so that the stent continues to be in close contact with and follow the inner surface of the vessel. Thus, in the area larger than the nominal diameter, the stent should only apply such a force that ensures contact between the stent and the vessel wall. The force should be selected so that the vessel does not have to "pull" on the stent during remodeling, but ideally as little physical action as possible is exerted on the vessel by the stent. In other words, instead of or in addition to the first and second expansion characteristics, the stent according to the invention can also be described in terms of the first and second radial forces F1, F2, and COF, respectively, or radial force levels to which the radial force falls in the first and second diameter regions. Furthermore, instead of or in addition to the first and second expansion characteristics, the stent according to the invention can be described by the radial force characteristic during expansion of the stent, which has at least one kink, at least one, preferably two, inflection points or at least one step. According to the invention, the radial force caused by the stent decreases sharply beyond the nominal diameter and drops to a very low level, preferably such that vessel remodeling does not occur or occurs only to a very small extent. Preferably, the second diameter range is at least 10% of a maximum diameter Dmax, so the second diameter range accounts for 10% or more of the total expansion. Preferably, the second diameter range is at least 15%, 20%, 25%, 30%, 40%, 50%, 60%, or 70% of the maximum diameter. Thereby it is preferably provided that the first diameter range comprises at most 90% of the maximum diameter Dmax, preferably 80%, further preferably 75%, 70%, 65%, 60%, 55%, or 50%.

It is further preferred that the radial force in the first diameter region drops to a first radial force level during expansion and drops to a second radial force level in the second diameter region, which is lower than the first radial force level. Preferably, the first radial force level is greater than the second radial force level by a factor, the factor being in a range from 2 to 20, preferably in a range from 2 to 10, more preferably from 3 to 10, more preferably from 4 to 10, more preferably from 5 to 9.

In a preferred further embodiment, a radial force diameter profile of the stent has a kink or step. A radial force-diameter profile represents the progression of the radial force starting from a crimped state to the maximum diameter plotted over the diameter. In conventional stents, a radial force-diameter profile has no kink or step; instead, the radial force decreases essentially continuously, in particular degressively, from the crimped state to the maximum diameter and then ends abruptly. The stent described herein has a radial force diameter profile having at least one kink, preferably at least two or more kinks. The radial force-diameter profile has at least one, preferably two inflection points plotted as a graph. Further preferably, the radial force-diameter profile in the first diameter range, starting from the crimped state during expansion, initially has a section with a first slope, then a section with a second slope, and in the second diameter region, starting from the nominal diameter, a third section with a third pitch and a fourth section with a fourth pitch, wherein the first pitch and is greater than the second pitch and the fourth pitch, and the third pitch is greater than the second pitch and the fourth pitch. The third slope may be greater than the first slope. The second slope may be greater than the fourth slope. The first slope is preferably greater than the second slope by at least a first slope factor, wherein the first slope factor is at least 2.0; 2.5; 3.0; 3.5; 4.0; 4.5; 5.0; 5.5; 6.0; 7.0; 8.0; 9.0; 10.0; 12.0; 15.0. Preferably, the third pitch is greater than the second and/or fourth pitch by at least a second pitch factor, the first pitch factor being at least 2.0; 2.5; 3.0; 3.5; 4.0; 4.5; 5.0; 5.5; 6.0; 7.0; 8.0; 9.0; 12.0; 15.0. Preferably, the radial force-diameter profile of the stent, starting from the crimped state to the expanded state, has the following course: in the first diameter range, first a pitch decrease followed by a pitch increase, then, upon transition, when passing into the second diameter range, a further decrease in pitch and, preferably, finally, a further increase in pitch. The progression can also be described as degressive-progressive-degressive. Further preferably, the first diameter region defines a first radial stiffness profile section, and the first radial stiffness profile section is degressive, regressive or linear. A degressive or regressive stiffness as the diameter of the stent increases provides a more rapid decrease in force as it expands. Preferably, the radial force in the first diameter region is substantially constant or only slightly decreasing over at least one section, and in the second diameter region is also substantially constant. This can be achieved by the radial stiffness being degressive or regressive.

According to a second aspect of the invention, the above-mentioned object is solved by a use of a self-expandable stent in a method according to any of the above-described preferred embodiments of a method according to the first aspect of the invention.

It should be understood that the stent described in the method and the use of the stent of the second aspect have identical and similar subaspects and features and the stent of the use according to the second aspect of the invention may have similar and identical features as the stent described with respect to the method of the first aspect of the invention.

In particular, the stent of the use according to the second aspect of the invention may have a proximal section and a distal section, said distal section being adapted and designed to be positioned adjacent the aneurysm sac and said proximal section being adapted and designed to be positioned away from said aneurysm sac, and wherein the distal section generates a higher radial force (in particular chronical radial outward force and/or radial resistive force) than said proximal section.

According to a third aspect of the invention, the above-mentioned object is solved by an imaging apparatus for imaging a placement position of a stent in an abdominal aorta of a subject. The imaging apparatus may comprise a representation providing unit for providing image data representing at least a portion of the abdominal aorta of the subject; an identification unit for identifying in said image data: (a) an abdominal aortic aneurysm (AAA) portion of the abdominal aorta having an aneurysm sac and an aneurysm neck, (b) a distal end of the aneurysm neck, (c) a lower renal artery, and/or (d) a first distance between a distal end of an lower renal aortic ostium and the distal end of the aneurysm neck, and/or a second distance between a proximal end of the lower renal aortic ostium and the distal end of the aneurysm neck. The imaging apparatus further may comprise a placement position providing unit for (i) comparing the first distance with a minimum stent length and in case the first distance is larger than the minimum stent length, selecting a stent length smaller than the first distance or larger than the second distance; and in case the first distance is smaller than the minimum stent length, selecting a stent length larger than the second distance; and (ii) for defining a stent placement position in accordance with the selected stent length with a distal stent end aligned with the distal end of the aneurysm neck. Further, the imaging apparatus may comprise a display for displaying the stent placement position in said image data.

It shall be understood that the planning method according to the first aspect of the invention and the imaging apparatus according to the third aspect of the invention comprises identical and similar subaspect which in particular are described in the above specification and the dependent claims. Insofar, reference is made to the above description of the panning method according to the first aspect of the invention.

BRIEF DESCRIPTION OF THE DRAWINGS

For a more complete understanding of the invention, the invention will now be described in detail with reference to the accompanying drawings. The detailed description will illustrate and describe what is considered as a preferred embodiment of the invention. It should of course be understood that various modifications and changes in form or detail could readily be made without departing from the spirit of the invention. It is therefore intended that the invention may not be limited to the exact form and detail shown and described herein, nor to anything less than the whole of the invention disclosed herein and as claimed herein after. Further, the features described in the description, the drawings and the claims disclosing the invention may be essential for the invention considered alone or in combination. In particular, any reference signs in the claims shall not be construed as limiting the scope of the invention. The wording “comprising” does not exclude other elements or steps. The word “a” or “an” does not exclude the plurality. The wording “a number of” items comprising also the number 1, i.e., a single item, and further numbers like 2, 3, 4 and so forth. In the accompanying drawings:

DETAILED DESCRIPTION OF THE INVENTION

Figure 1:
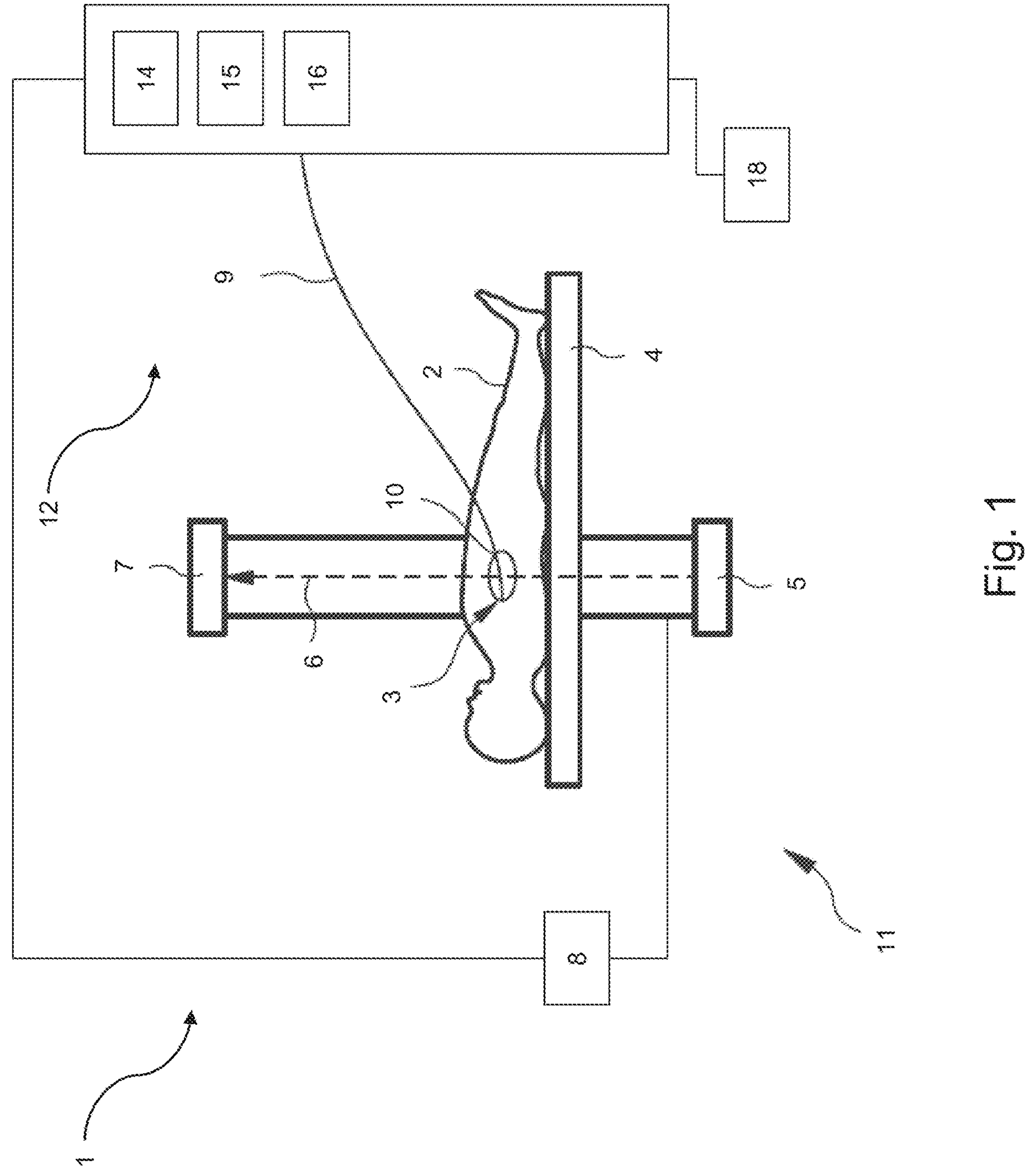
FIG. 1 shows schematically and exemplary an embodiment of an imaging apparatus.

FIG. 1 shows schematically and exemplarily an interventional system 1 for moving a catheter 9 within a vascular structure 3 in a person 2 lying on a support means 4 like a table, in order to perform an interventional procedure. The vascular structure 3 in this case in an abdominal vascular structure with an abdominal aortic aneurysm (AAA) 10 on which a treatment shall be carried out. The catheter 9 may be used to place a stent 20 in a stent placement position 22 which is to be defined by a planning method before. The interventional procedure is not part of this invention. The invention disclosed herein is only directed to the definition and determination of the stent placement position. The interventional procedure is not necessary for defining or determining the stent placement position.

The interventional system 1 in this embodiment comprises an imaging apparatus 12 for imaging the placement position 22 of the stent. The imaging apparatus 12 comprises a representation providing unit 14 for providing image data 26 representing at least a portion of the abdominal aorta 24 of the patient 2. The image data 26 at least comprises a representation of the aneurysm sac 27 and the aneurysm neck 28 adjacent to the aneurysm sac 25. The image data 26 may comprise a two-dimensional and/or three-dimensional representation in a pre-interventional image like a pre-interventional computed tomography, magnetic resonance image, a pre-interventional ultrasound image or other two- and/or three-dimensional image modality. In FIG. 1, a computed tomography device 11 is shown, having an x-ray source 5 for emitting x-rays 6 traversing the person 2 lying on the support means 4. The computed tomography device 11 further comprises an x-ray detector 7 for detecting x-rays 6, after having traversed the person 2. The x-ray source 5 and the x-ray detector 7 are mounted on a C-arm. Also shown is a catheter 9, which can be used to place the stent 20 in the stent placement position 22 as described later. The x-ray detector 7 is adapted to generate detection signals being indicative of the detected x-rays 6, wherein the detection signals are transmitted to a computed tomography control unit 8, which is adapted to control the computed tomography device 11, the x-ray source 5 and the x-ray detector 7 to generate two-dimensional projection images depending on the received detection signals. The generated images can be used as image data 26, or image data 26 is generated based on the generated computed tomography image data.

Figure 2:
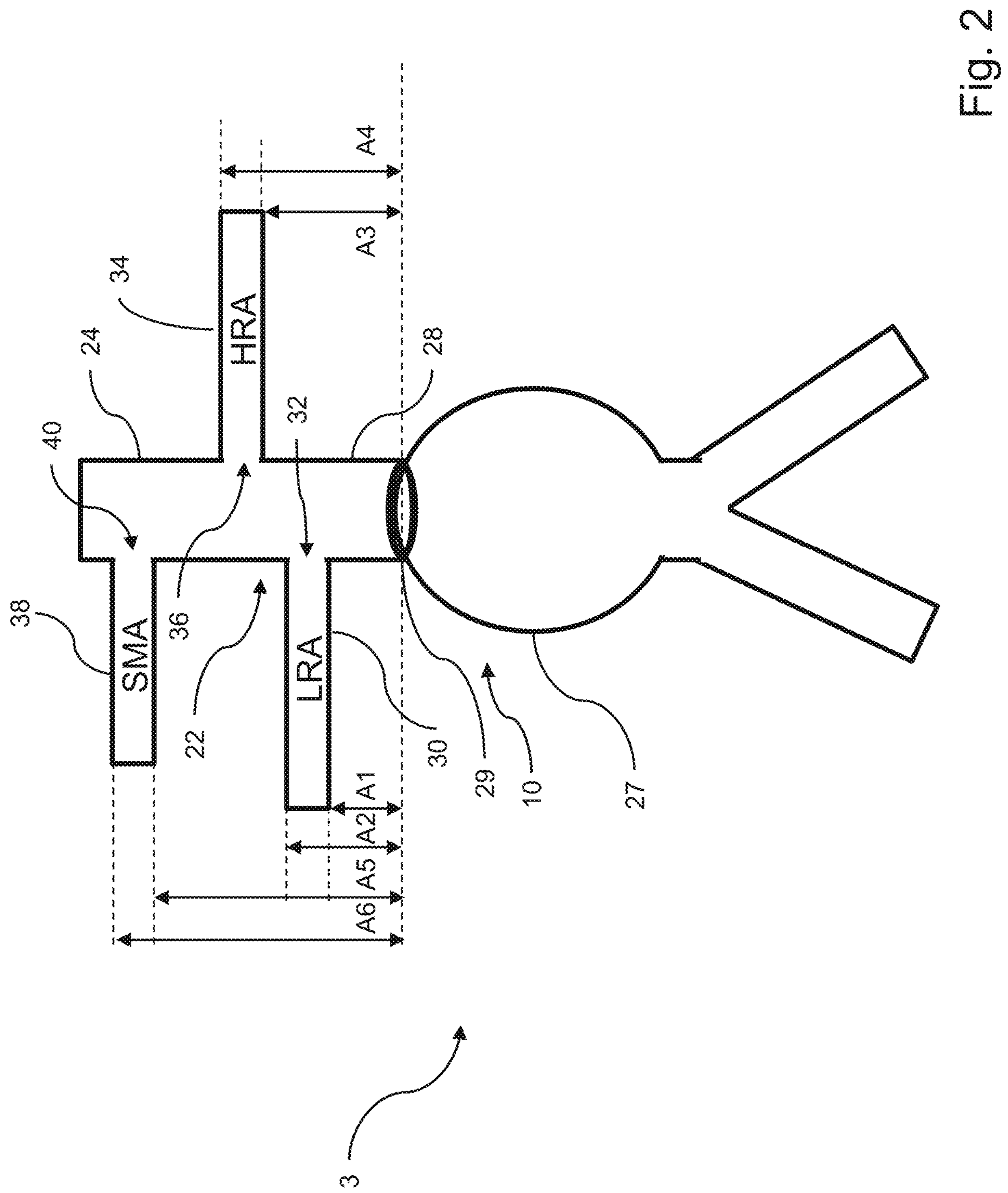
FIG. 2 shows schematically and exemplary an abdominal aortic aneurysm.
Figure 4:
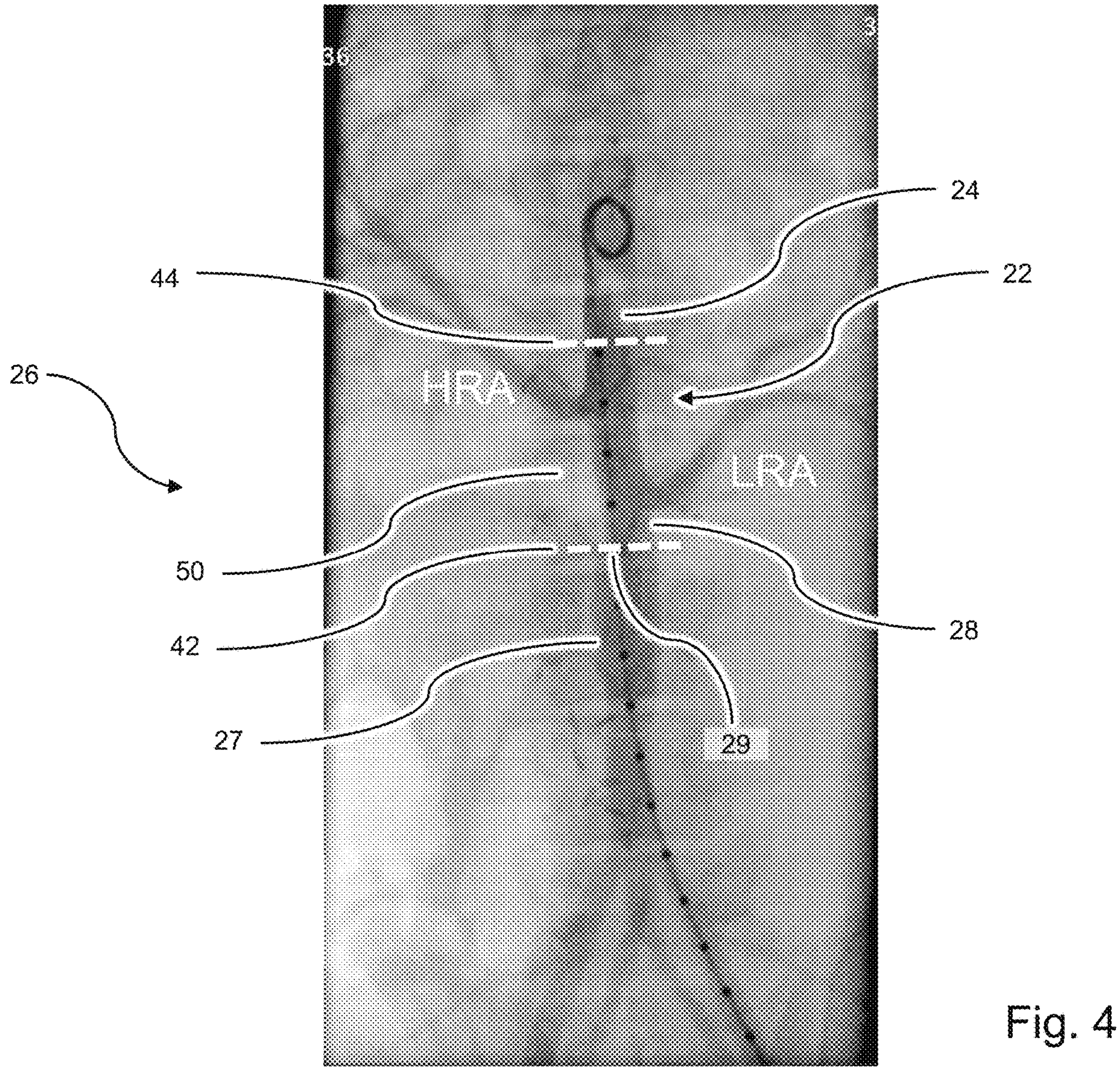
FIG. 4 shows schematically and exemplary a representation of image data with indicated stent placement position.
Figure 5:
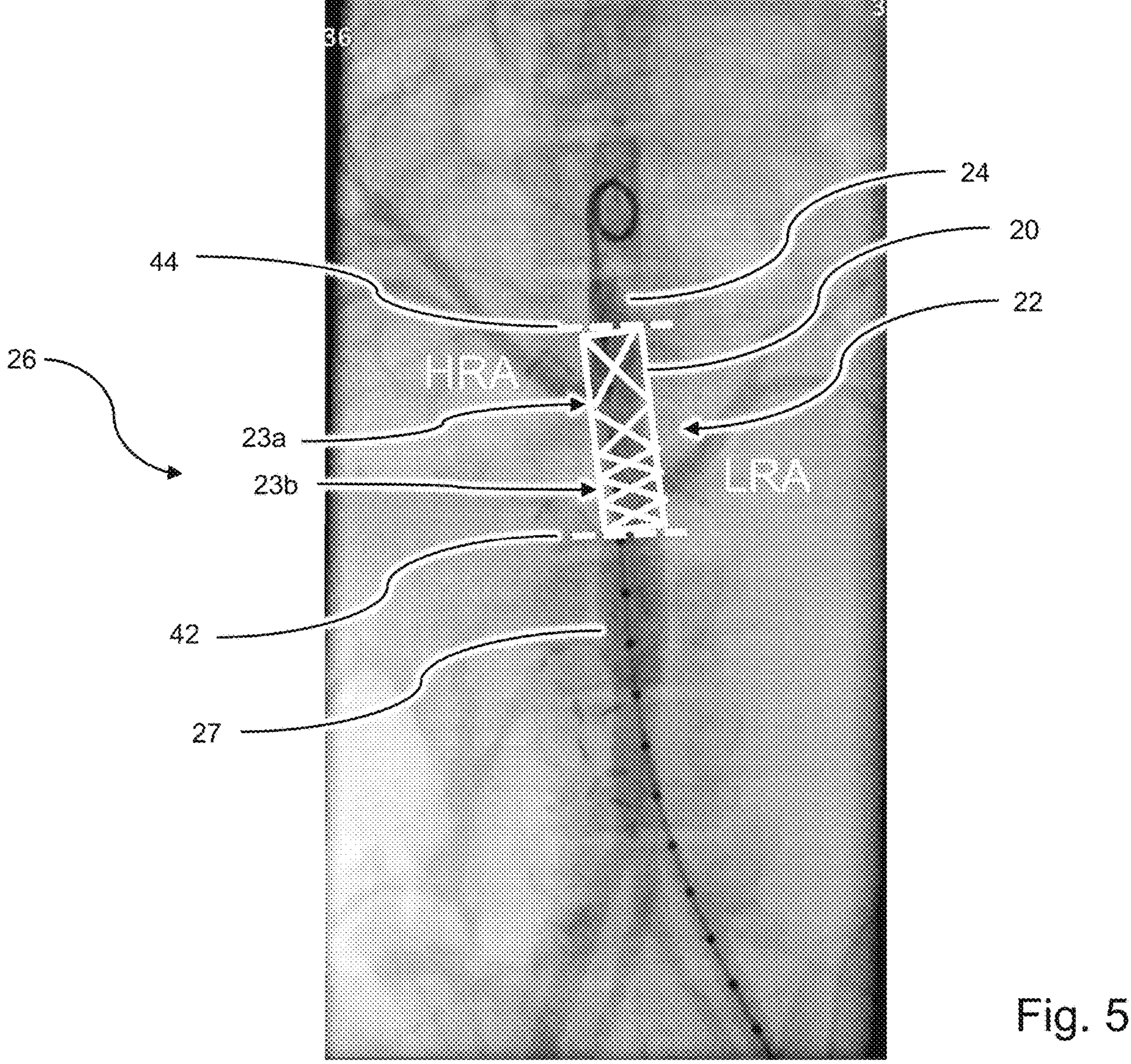
FIG. 5 shows schematically and exemplary the representation of FIG. 4 with indicated stent in the stent placement position.

The imaging apparatus 12 further comprises an identification unit 15 for identifying in said image data 26: the abdominal aortic aneurysm (AAA) 10 of the abdominal aorta 24 having an aneurysm sac 27 and an aneurysm neck 28, a distal end 29 of the aneurysm neck 28 and a lower renal artery (LRA) 30 (see FIG. 2). Further, the identification unit 16 is adapted and structured for identifying a first distance A1 between a distal end of a lower renal aortic ostium 32 and the distal end 29 of the aneurysm neck 28, and a second distance A2 between a proximal end of the lower renal aortic ostium 32 and the distal end of the aneurysm neck 28. The identification unit 16 may be adapted and structured to identify these structural elements using image recognition methods. In particular such image recognition methods may include recognizing edged in the image data and identifying based on the edges said structures. The identification unit 15 may also be adapted and structured to identify the structural elements using annotations as shown in FIGS. 4 and 5 with the letters "LRA" and "HRA" which can be shown on the display. The identification unit 15 may be adapted and structured to provide this identification to the user as a proposal and the user may be requests to confirm the correct identification of the elements. The user may then be able to modify the determined position of the elements so that all elements and distances are correctly identified in said image data 26. Representations of annotations for identifying one, some or all of the structural elements and distances may be added to the image data 26 and/or stored in association with the image data 26.

The identification unit 15 further is preferably adapted and structured to identify in said image data a higher renal artery (HRA) 34, and a third distance A3 between a distal end of a higher renal aortic ostium 36 and the distal end 29 of the aneurysm neck 28. Further, the identification unit 15 preferably is adapted and structured to identify a fourth distance A4 between a proximal end of the higher renal aortic ostium 36 and the distal end 29 of the aneurysm neck 28. Again, it is preferred that the third and/or fourth distance, as well as the position of the higher renal artery (HRA) 34 are identified in the image data 26, or that a representation is generated which is stored in association with the image data 26 in a storage.

Furthermore, it is preferred that the identification unit is adapted and structured to identify a superior mesenteric artery (SMA) 38. Further, a fifth distance A5 between a distal end of a superior mesenteric aortic ostium 40 and the distal end 29 of the aneurysm neck 28, as well as preferably a sixth distance A6 between a proximal end of the superior mesenteric aortic ostium 40 and the distal end of the aneurysm neck 28 is identified. Again, those identified elements can be represented in the image data similar as shown in FIGS. 2 to 5. In particular, the sixth distance A6 is not necessarily to be identified, since the stent 20 should not extend in a proximal direction closer to the heart than the distal end of the superior mesenteric aortic ostium 40.

The imaging apparatus 12 may also comprise a placement position providing unit 16. The placement position providing unit 16 is preferably adapted and structured for comparing the first distance A1 with a minimum stent length. The minimum stent length may be dependent on the sent manufacturer and may be stored in a storage associated with the imaging apparatus 12 or may be set by a user. In case the first distance A1 is larger than the minimum stent length, a stent length smaller than the first distance A1 or larger than the second distance A2 is selected. This selection can be done automatically, based on a suggestion of the placement position providing unit 16 or based on a user selection. In case the first distance A1 is smaller than the minimum stent length, a stent length larger than the second distance A2 is selected. Again, this selection can be done automatically, based on a suggestion of the placement position providing unit 16 or based on a user selection. Subsequently, the stent placement position 22 is determined in accordance with the selected stent length with a distal stent end aligned with the distal end 29 of the aneurysm neck 28.

In case it is determined that the minimum stent length or a length of a stent which shall be selected is greater than the second distance A2, this stent length is compared to the third distance A3 and the fourth distance A4. In case it is smaller than the third distance, the stent 20 can be selected accordingly, in case it is larger than the third distance but smaller than the fourth distance, another stent with a stent length greater than the fourth distance A4 shall be selected. This can be done by providing a respective suggestion to the user via a display 18 and a request that the user shall confirm the selected stent length. For example, a respective representation of a stent may be shown to the user with a dialogue asking the user whether this selection is okay or not. The user may be given the opportunity to select another stent with a different stent length. The stent placement position 22 is then defined as the position of the stent 20 with the distal end of the stent 20 being aligned with the distal end 29 of the aneurysm neck 28, i.e., the distal end of the stent 20 being aligned with the proximal end of the aneurysm sack 27.

Figure 3:
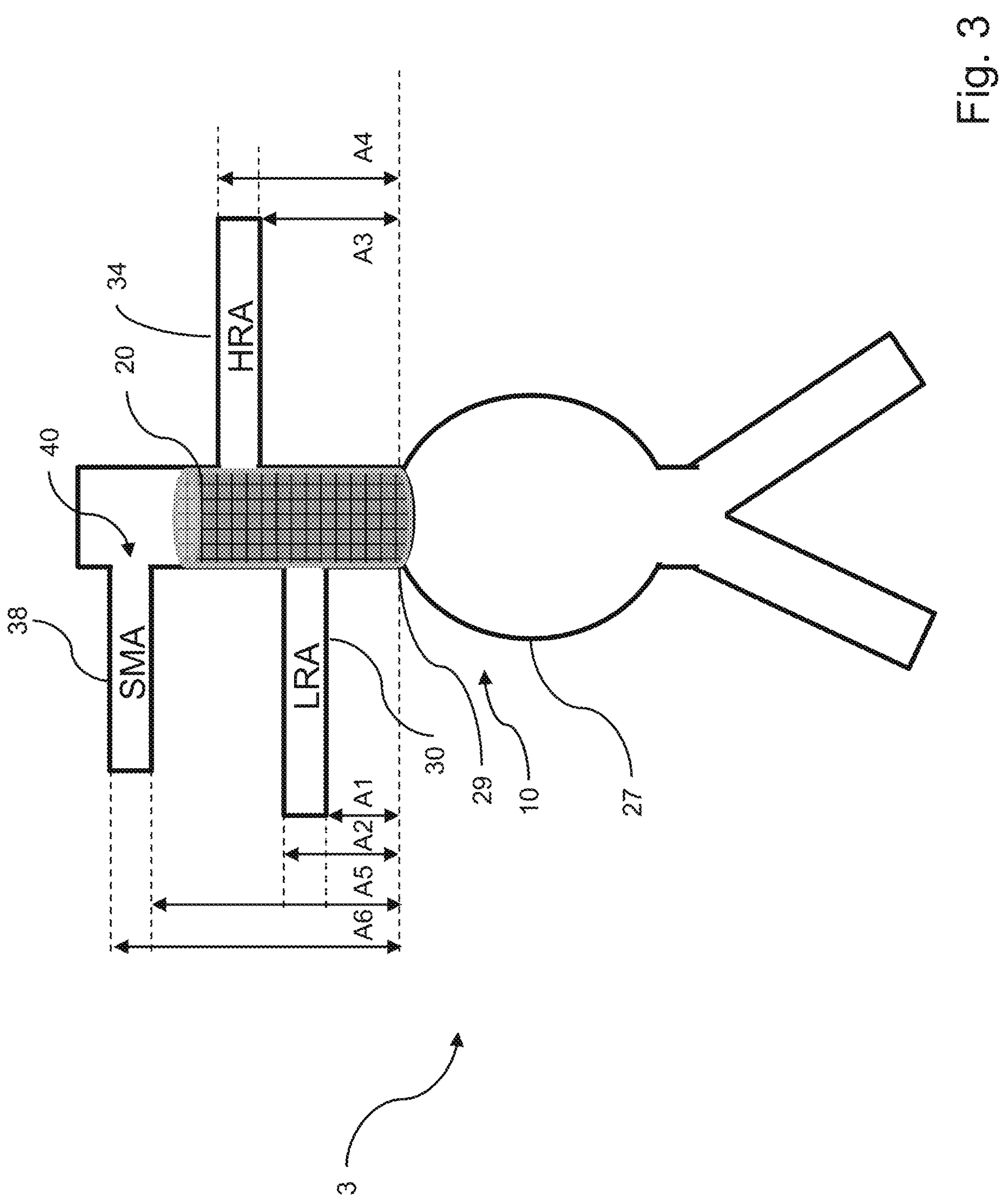
FIG. 3 shows schematically and exemplary an abdominal aortic aneurysm with stent placed in the stent placement position.

A stent 20 is shown in FIG. 3 positioned in the stent placement position 22 as defined before. The stent 20 in the exemplary embodiment shown in FIG. 3 has a length which is greater than the fourth distance, but smaller than the fifth distance. Thus, the proximal end of the stent 20 is positioned between the higher renal artery 34 and the superior mesenteric artery 38 and is positioned such that it will not kink into one of the aortic orifices. Moreover, it is placed such that it is as adjacent to the aneurysm sack 27 as possible so that aneurysmal growth can be reliably prevented.

The image apparatus 12 or the interventional system 1 may comprise a display 18 for displaying the stent placement position 22 in said image data 26. The display 18 may for example show a view as shown in FIGS. 4 and 5. In particular, in FIG. 4 the stent placement position 22 can be seen. The stent placement position 22 is indicated by means of a distal dashed line 42 and a proximal dashed line 44. The distal dashed line 42 and the proximal dashed line 44 are represented in the image data 26 and can be shown together with the image data 26 on the display 18. The distal dashed line 42 is positioned at the distal end 29 of the aneurysm neck 28, and the proximal dashed line 44 is positioned according to the stent length of the selected stent, in the embodiment shown in FIG. 4 between the fourth and fifth distance A4, A5, which are not shown in FIGS. 4 and 5; rather in FIGS. 4 and 5, only the higher renal artery and the lower renal artery HRA, LRA are indicated. The distal dashed line 42 and the proximal dashed line 44 are exemplary only and other structures can be used to identify the stent placement position 22. Other suitable structures include arrows, highlighted portions, rectangles, or the like. Important is that the stent placement position can be reliably shown in the image data. Preferably, the stent placement position 22 is linked to a landmark 50; in the example of FIG. 4, the landmark 50 is a bone of the spine. This is beneficial, since the vessel structure of the abdominal aorta 24 may not be seen in any type of image data, for example in x-ray image data, the vessel structure of the abdominal aorta 24 may not be visible, so that a surgeon may not be able to navigate on the vessel structure only, but will also use the landmark 50 and the indicated stent placement position 22 for releasing the stent 20 properly. A released stent 20 can be seen in FIG. 5, schematically, being place in the stent placement position 22.

The stent 20 has at least a proximal section 23*a* and a distal section 23*b*, which in this case may provide different radial forces and/or different radial stiffness to the vessel. In FIG. 5 this is indicated by the different size of the "x"-pattern of stent 20. This will be described in more detail with respect to FIG. 15.

Figure 6:
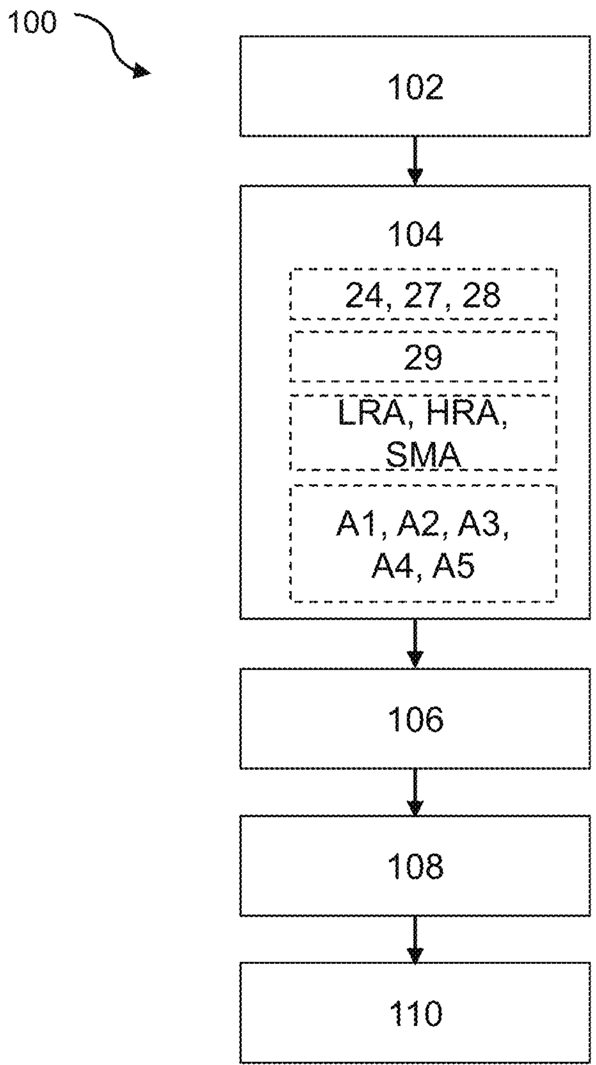
FIG. 6 shows a flowchart exemplarily illustrating an embodiment of a planning method for defining a placement position of the stent.

FIG. 6 illustrates a planning method 100 for defining the stent placement position of a stent in an abdominal aorta as described above. In a first step 102, image data 26 is provided, representing at least a portion of the abdominal aorta 24 of the subject 2. Step 104 is an identifying step, in which in said image data 26 which has been provided in step 102, an abdominal aortic aneurysm portion of the abdominal aorta 24 having an aneurysm sack 27 in an aneurysm neck 28 is identified. Further, a distal end 29 of the aneurysm neck 28 is identified, as well as a lower renal artery and a higher renal artery 34. Optionally but preferably, also a superior mesenteric artery 38 is identified. When both structural features have been determined, in particular the different distances can be identified, a first distance A1 between a distal end 29 of a lower renal aortic ostium 32 and the distal end 29 of the aneurysm neck 28, and a second distance A2 between a proximal end of the lower renal aortic ostium and the distal end 29 of the aneurysm neck 28, a third distance A3 between a distal end of a higher renal aortic ostium 36 and the distal end 29 of the aneurysm neck 28, a fourth distance A4 between a proximal end of the higher renal aortic ostium 36 and the distal end of the aneurysm neck 28, as well as preferably a fifth distance A5 between a distal end of a superior mesenteric aortic ostium 40 and the distal end 29 of the aneurysm neck 28. Preferably, also a sixth distance between a proximal end of the superior mesenteric aortic ostium 40 and the distal end 29 of the aneurysm neck 28 is identified. In step 106, the identified and determined distances A1, A2, A3, A4, A5 are compared to a minimum stent length, and are known stent lengths of suitable stents. When a suitable stent has been found with a suitable stent length, a stent placement position can be determined and identified in step 108. The determined stent placement position can be identified in the image data 26 and viewed on a display 18 in step 110. This image data with the stent placement position identified can be used in a subsequent interventional procedure, to release the stent in the correct position.

FIGS. 7 to 14 now show different embodiments of a stent 20 which can beneficially be used in the method and system described above.

Figure 7:
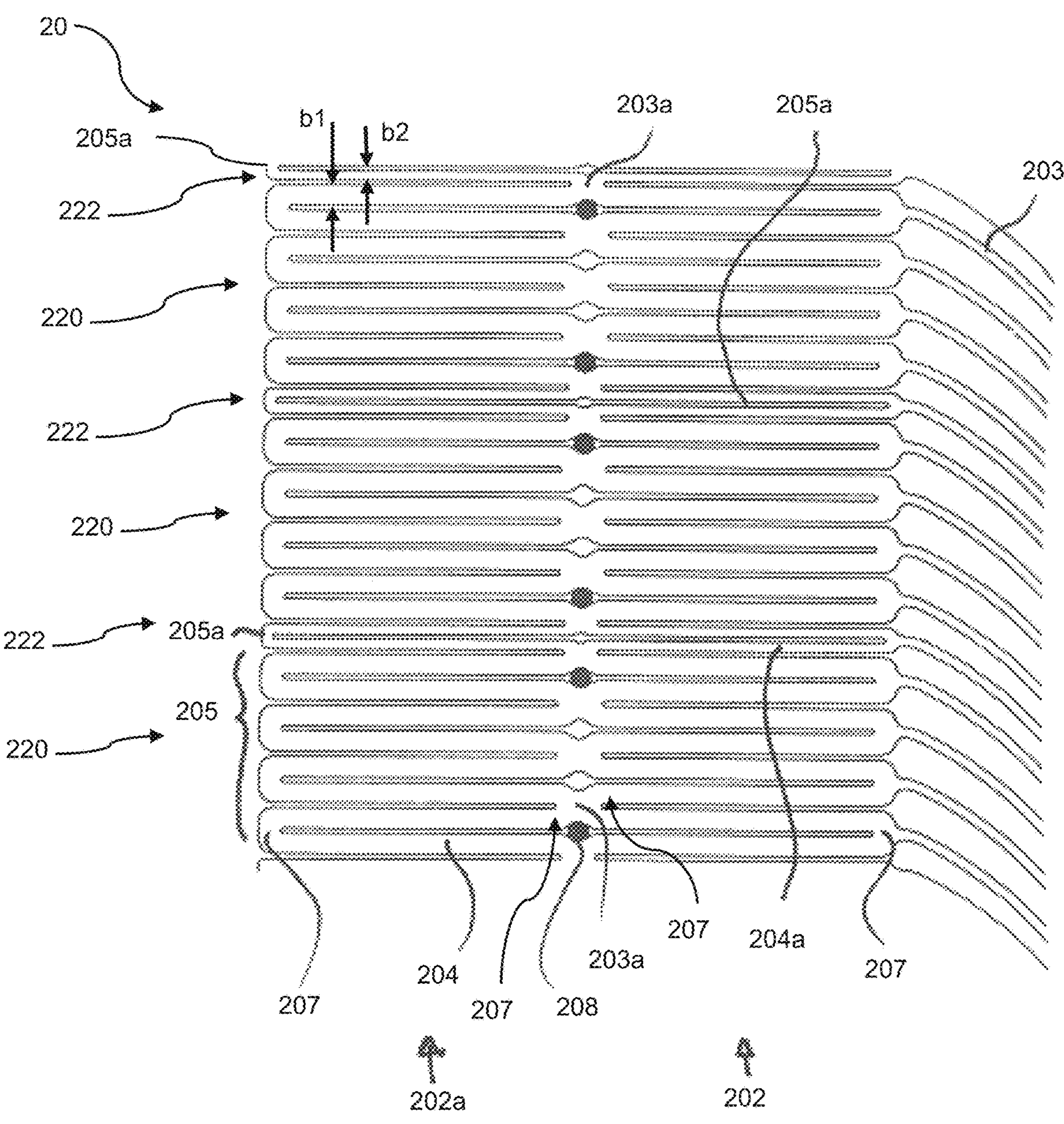
FIG. 7 shows the end region of a stent in planar view, FIG. 8 schematically shows a ring segment of a stent in expanded state, FIG. 9 schematically shows a ring segment of a stent in a post-expanded state (expansion reserve)

FIG. 7 shows the end region of an unexpanded stent 1 according to the invention (self-expanding) in planar representation. It is to be understood that the stent 1 generally has a tubular structure, but here for better illustration it is shown flat, i.e., only the surface of the otherwise tubular stent.

In the embodiment shown in FIG. 7, the stent 20 has two ring segments 202, 202*a*, which are arranged axially (with reference to FIG. 7 horizontally) next to and adjacent to each other. The individual ring segments 202 and 202*a* are connected to their adjacent ring segments 202 and 202*a*, in this case by connecting webs 203. That is, with reference to FIG. 7, to the right of the ring segment 202, one or more ring segments (not shown) may be adjacent, which are connected to the ring segment 202 via the connecting webs 203. The connecting webs 203 primarily secure the axial alignment of the individual ring segments 202, 202*a*, but do not themselves exert any significant radial force. In the stent section shown, the end ring segment 202*a* is further connected to the adjacent ring segment 202 directly at contact points 203*a* of the peaks or crowns 207, which are axially adjacent and opposite each other. The individual struts 204, 204*a* of the ring segments 202 and 202*a* meander so that they spread in a zigzag pattern during expansion. All struts 204 and 204*a* are connected to their neighbouring struts 204 and 204*a* by peaks or crowns 207.

The stent 20 is formed such that the ring segments 202, 202*a* have a first expansion characteristic in a first diameter range D1 (cf. FIGS. 10, 11) smaller than the nominal diameter DN, and have a second expansion characteristic in a second diameter range D2 larger than the nominal diameter DN, the first and second expansion characteristics being different. In this way, the stent 20 is capable of providing in the first diameter region D1 a first chronic outward force COF1, preferably a first radial force in a first region, preferably, and in the second diameter region D2 a second chronic outward force COF2, preferably a second radial force in a second region. This will be described in more detail below and also with reference to FIGS. 8-11.

In the first embodiment of the stent 20 shown in FIG. 7, each of the ring segments 202, 202*a* has a plurality of circumferential segments, in this case a total of three first circumferential segments 220 and three second circumferential segments 222, each arranged alternately around the circumference of the respective ring segment 202, 202*a*. In this sense, the second circumferential segments 222 are evenly distributed around the circumference, in this case each offset from the other by 120°. A uniform distribution is advantageous to achieve a uniform expansion of the stent 20. More or less than three first and three second circumferential segments 220, 222 may also be provided. In particular, a stent 20 with only one second circumferential segment 222 may likewise be according to the invention. In further embodiments, one or more third circumferential segments (not shown) may also be provided to achieve a further gradation of the radial force.

In the stent 20 shown in FIG. 7, six struts 204*a* of smaller width b2 are arranged in each ring segment 202 and 202*a*. These struts 204*a* of smaller width b2 form in pairs the second circumferential segments 222, also called "soft stent segments 205*a*". In the embodiment example shown here, the first circumferential segments 220, also called "hard stent segments 205", each have eight struts 204 or four pairs of struts. The struts 204 of the first circumferential segments 2020 have a first width b1. During normal expansion from a crimped state to nominal diameter, only the first circumferential segments 220 (hard stent segments 205) are expanded, while the second circumferential segments 222 (soft stent segments 205*a*) remain in their closed state.

In the case shown, the struts 204*a* of the second circumferential segments 222 have approximately the half width of the struts 204 of the first circumferential segments 220. The force required to expand the second circumferential segments 222 is correspondingly less and can be readily applied by an expanding vessel (passive expansion). Alternatively, the second circumferential segments 222 can have an expansion reserve provided by the shaping to allow active expansion when the vessel expands/remodels. The thickness in radial direction as well as the length in axial direction measured of the individual struts 204, 204*a* is the same for all struts 204, 204*a* in this embodiment; the stent 20 is preferably cut from a uniform tubular material. The first width b1 of the first struts 204 of the first circumferential segments 220 preferably defines a first radial stiffness, and the second width b2 of the second struts 204*a* of the second circumferential segments 222 preferably defines a second radial stiffness. Accordingly, in the embodiment of FIG. 7, the radial stiffness, and also a radial force-diameter profile is predetermined by the shape and design of the struts 204, 204*a* and can be adjusted by them. Preferably, the first width b1 of the first struts 204 of the first circumferential segments 220 is larger by a factor than the second width b2 of the second struts 204*a* of the second circumferential segments 222. A ratio b1/b2 is preferably in a range of 1.5 to 5, preferably 1.5 to 4, more preferably 2 to 3.5.

The peaks or crowns 207 are the attachment points of the connecting bars 203 and the rotation or bending points during expansion or crimping of a self-expanding stent 20.

The points 208 shown are the fixation points where the stent 20 is fixed to a support during shaping in such a way that the soft stent segments 205*a* remain closed in nominal diameter.

A central region of stent 20, which is not shown, can be connected to the right end region shown via the connecting webs 203, which can have a conventional design except for the soft stent segments 205*a*. However, stent 20 can also be formed only from the two ring segments 202, 202*a* and in this respect have no connecting webs 203. It is also conceivable that instead of the connecting webs 203, one or more further ring segments are connected directly via contact points 203*a* at the right axial end with reference to FIG. 7, which can be formed identically or similarly to the ring segments 202, 202*a*.

Figures 8, 9:
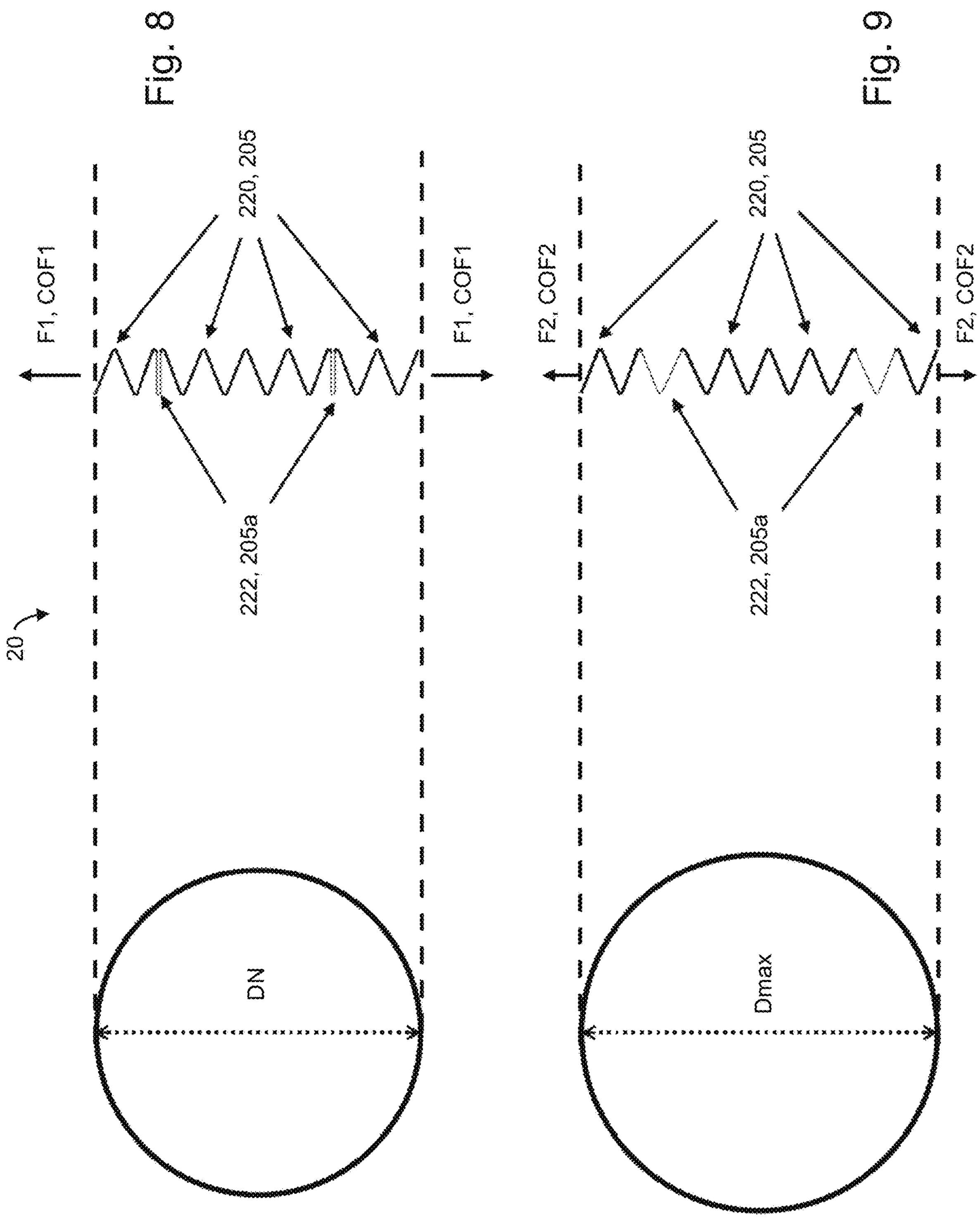

FIG. 8 schematically shows a stent 20 with its nominal diameter DN after implantation in a vessel, in particular in the stent placement position 22 as described above. The depicted ring segment 202 shows the expanded first circumferential segments 220 (hard stent segments 205) in an open state, while the second circumferential segments 222 (soft stent segments 205*a*) are still closed. F1 denotes the high radial forces of the first circumferential segments 220 (hard stent segments 205).

Compared to the embodiment of FIG. 7, FIGS. 8 and 9 each show only one ring segment 202. It should be understood, however, that the embodiment of FIGS. 6 and 9 may likewise comprise two or more ring segments 202, 202*a*. In this respect, the illustration with only one ring segment 202 in FIG. 8, 9 serves illustrative purposes in particular. While FIG. 7 shows the crimped state of stent 20 in which it is compressed to a minimum diameter Dmin (cf. also FIGS. 10-12) in order to be implanted at this minimum diameter Dmin in the crimped state. In the crimped state (cf. FIG. 7), the single struts 204, 204*a* are essentially parallel to each other. In the expanded state, struts 204, 204*a* are at an angle to each other and spanning a space or cells between them.

When expanding to the nominal diameter DN (FIG. 8), only the first circumferential segments 220 are fully expanded, while the second circumferential segments 222 are still closed or in a partially crimped state. In the fully expanded state of the first circumferential segments 220, the first circumferential segments 220 no longer exert any further radial force. A radial stiffness of the second circumferential segments is preferably selected such that a second radial force F2, which can be caused by the second circumferential segments 222, is substantially lower than a first radial force F1, which is caused by the first circumferential segments 220. Moreover, the second radial stiffness of the second circumferential segments 222 is selected such that the second radial force F2 caused by them is so small that an expansion of the vessel does not occur. In this respect, the second circumferential segments 222 are held closed by the first circumferential segments 220 up to the nominal diameter DN; the second circumferential segments 222 cannot expand against the first radial force F1 provided by the first circumferential segments 220, since the second radial force F2 developed by the latter is too low.

FIG. 9 now schematically shows stent 20 with its maximum diameter Dmax after expansion of the vessel and complete expansion of the first circumferential segments 220. The depicted ring segment 202 shows the expanded first circumferential segments 220 in the open state, as shown in FIG. 8, and the likewise expanded second circumferential segments 222, which have followed the vessel expansion. F2 denotes the lower radial forces of the second circumferential segments 222 responsible for the post-expansion.

After stent 20 has expanded to the nominal diameter DN by the radial force developed by the first circumferential segments 220 and second circumferential segments 222, there may still be further deflection of the vessel wall and ultimately further expansion of the vessel (so-called remodeling). Stent 20 still allows a force to be applied in a diameter range D2 larger than the nominal diameter DN, namely a second permanent outward force (radial force) COF2. In the embodiment shown in FIGS. 1 to 3, this is realized by means of the second circumferential segments 222, which have only such a stiffness (second radial stiffness) that they develop the second radial force F2. The second radial force F2 is chosen to be low enough to prevent further expansion or remodeling of the vessel. The second radial force F2 is preferably selected in a range that only allows the vessel wall to be followed by stent 20.

At the maximum diameter Dmax, the second circumferential segments 22 are also fully expanded. In the case that the second circumferential segments 22 are designed to develop a radial force F2=0, the maximum diameter is defined in particular by the diameter beyond which a radial force acts inwards, i.e., the vessel would have to pull on stent 20 during further remodeling. In the event that the second circumferential segments 222 are designed to provide a radial force F2>0, the maximum diameter is defined in particular by the diameter at which stent 20 is in a relaxed position. Here, exceeding it would again cause a radial force to act inwardly, meaning that the vessel would have to pull on stent 20 during further remodeling. However, the second radial stiffness of the second circumferential segments 222 is preferably selected in such a way that there is no influence on the vessel wall, be it by a substantial radial force outwards or a substantial radial force inwards. A growth of the vessel beyond the nominal diameter DN is thus possible, even without loosening of stent 20, and a contraction of the vessel smaller than the nominal diameter DN is effectively avoided.

Figure 10:
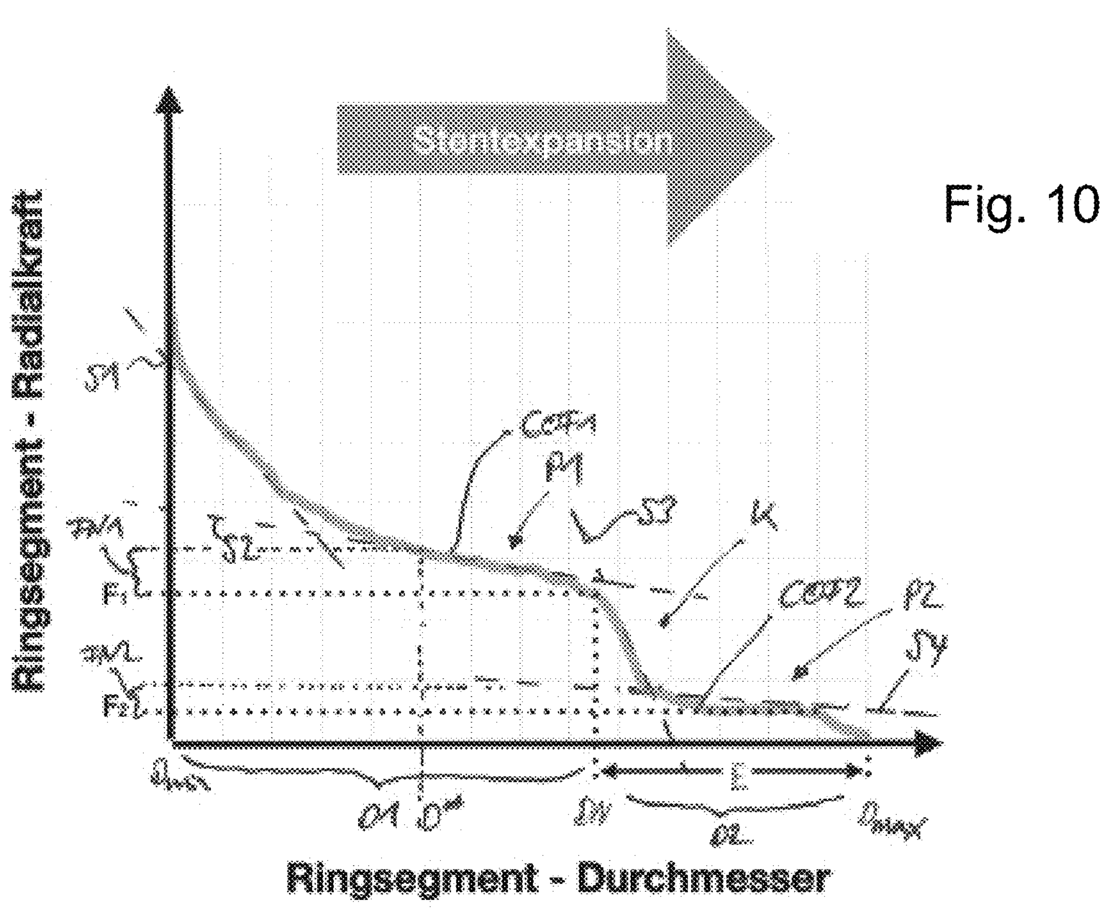
FIG. 10 shows a diagram illustrating the relationship between radial force and expansion/diameter of a stent.

FIG. 10 shows the radial force curve of a stent 20 according to FIG. 7 as a function of the degree of expansion or diameter. After implantation, stent 20, which is self-expanding, expands to the nominal diameter DN with decreasing radial force and exerts a first radial force F1 in a first area. The nominal diameter is reached at DN. Exclusively, during remodeling of the vessel, the maximum diameter Dmax is reached. During this post-expansion, the reduced second radial force F2 acts in a second radial force range. Range E denotes the expansion reserve.

The first chronical outward force COF1 is defined here by the area in which stent will or may come into contact with the vessel during expansion. In FIG. 10, exactly one force F1 is exerted at the nominal diameter DN. However, if the vessel is slightly smaller than the nominal diameter DN, a slightly higher radial force is exerted. Stent 20 should be designed to contact the vessel in a region where the first chronical outward force COF1 is at a first plateau P1, i.e., between the diameter D* and the nominal diameter DN. In this range, the first chronical outward force COF1 is at a first radial force level FN1.

From the minimum diameter Dmin in the crimped state of stent 20, the radial force exerted decreases rapidly until, approximately halfway through the first diameter range D1 (at D*) between the minimum diameter Dmin and the nominal diameter DN, it reaches a level in the range of a first radial force level FN1, which can be regarded as approximately constant. Up to this point, the radial force decreases degressively. Stent 20 has a first expansion characteristic up to this point, namely a degressive one. The vessel is radially expanded by the force of stent 20 up to the nominal diameter DN. It can be inferred from FIG. 10 that the radial force decreases stepwise from the nominal diameter DN to a region of a second radial force level FN2, and in particular to the second radial force F2, which in turn can be understood as essentially constant in the region of the second radial force level FN2. Stent 20 can thus exert a second chronical outward force COF2. In the second diameter region D2, the radial force thus again decreases degressively and stent 20 accordingly has a second expansion characteristic. This is different from the first one, since the degree of decrease and the force level reached is different. The second chronical outward force COF2 provided is so small that the vessel is not further actively expanded by stent 20, rather stent 20 merely gently follows any remodeling of the vessel without significant force. The second diameter area D2, larger than the nominal diameter DN thus represents an expansion reserve E. As can also be inferred from FIG. 10, the radial force-diameter curve has a kink K1 or step in the region of the nominal diameter DN. In this region, the curve no longer runs steadily and asymptotically, as is known from conventional stents, but drops suddenly to the second radial force level FN2. In the example shown in FIG. 10, the first radial force F1 is about 5 to 6 times the second radial force F2.

Furthermore, gradients S1 to S4 are drawn as straight lines in FIG. 10. In the first diameter range D1, the radial force asymptotically approaches the straight line S2, which indicates a second gradient S2. In the second diameter range D2, the radial force asymptotically approaches the straight line S4, which indicates a fourth gradient S4. Both the second and fourth slopes S2, S4 are small and can be understood as essentially linear. Starting from the crimped state at Dmin, the radial force initially drops sharply with a slope S1, which is tangentially plotted here, and then drops from the diameter D* to the nominal diameter DN with the second slope S2. The first slope S1 is significantly larger than the second slope S2. When expanding beyond the nominal diameter DN, the radial force then drops again first with a larger gradient S3, and then again with a smaller gradient S4.

Figure 11:
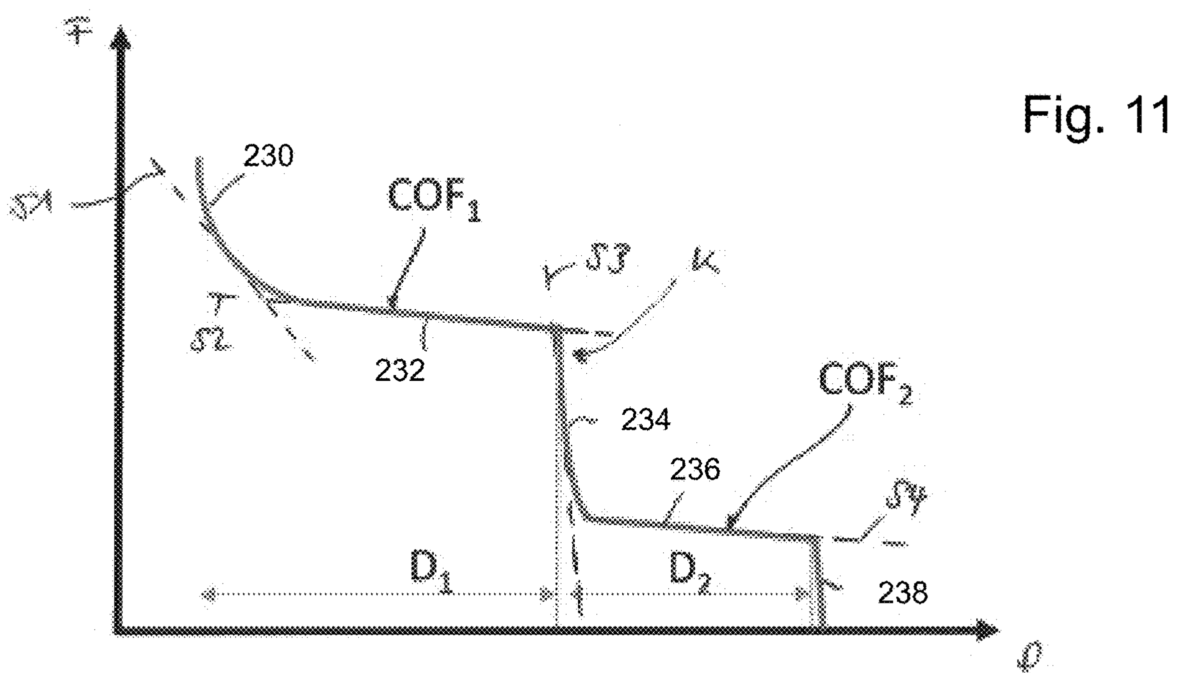
FIG. 11 is another diagram illustrating the relationship between radial force and expansion/diameter of the stent.

FIG. 11 shows a further radial force-diameter curve of stent 20 usable in the invention. Again, from the minimum diameter Dmin in the crimped state of stent 20, the radial force, plotted on the ordinate, initially drops degressively in a first section 230 until the radial force reaches a first plateau 232 in the first diameter range D1. On this first plateau 232, which in the embodiment example of FIG. 11 corresponds to the first radial force level FN1, a constant force does not necessarily have to be exerted completely over the first diameter range D1, although this is desirable. The first chronical outward force COF1 generated in this region remains approximately constant as the stent expands to the nominal diameter DN, dropping slightly with slope S2. When the stent 1 expands beyond the nominal diameter DN, the radial force then drops abruptly in a step 34 with the third slope S3, which does not necessarily have to be linear, but can also be degressive. Preferably, the force drop is as steep as possible and the radial force drops from the level of the first chronical outward force COF1 to a substantially lower level as immediately as possible when the nominal diameter DN is exceeded. In the embodiment shown in FIG. 11, the radial force drops to a second plateau 236, which here again represents a substantially constant radial force analogous to the first plateau 232, which here is designated as the second chronical outward force COF2. The level of the second chronical outward force COF2 remains essentially constant over the second diameter range D2, dropping slightly with the fourth slope S4. When the maximum diameter Dmax is reached, the radial force then drops to around zero. This again takes place in a step 238 in the embodiment shown here, but could also taper off more flatly, linearly or degressively. The first chronical outward force COF1 in the example shown in FIG. 11 is 3 to 3.5 times the second chronical outward force COF2.

Figure 12C:
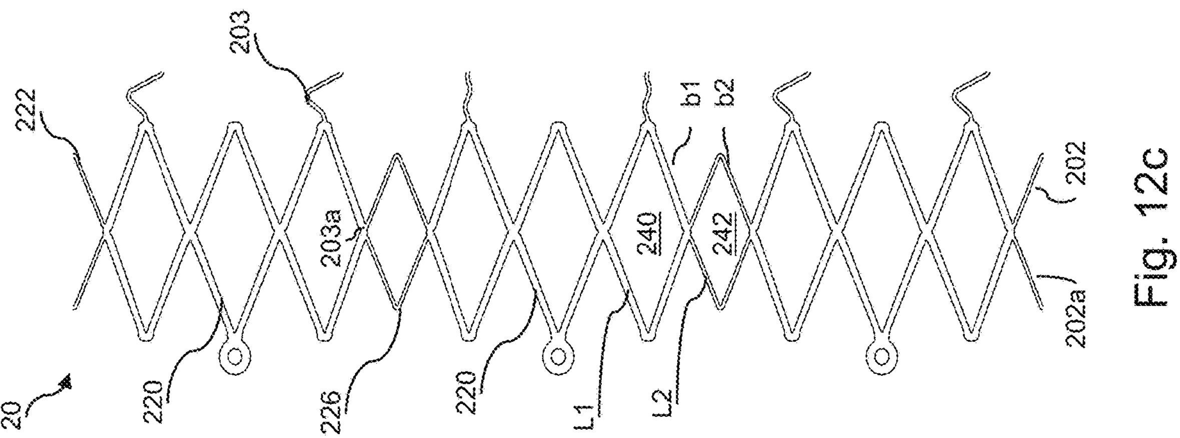
FIGS. 12*a* to 12*c* show an annular segment of the stent in a crimped state, at nominal diameter and at maximum diameter.
Figure 12B:
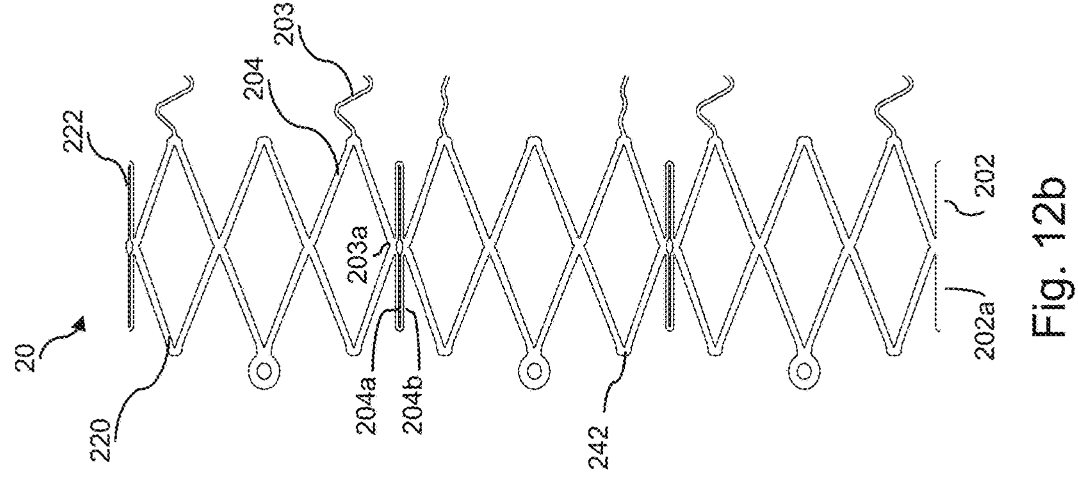
Figure 12A:
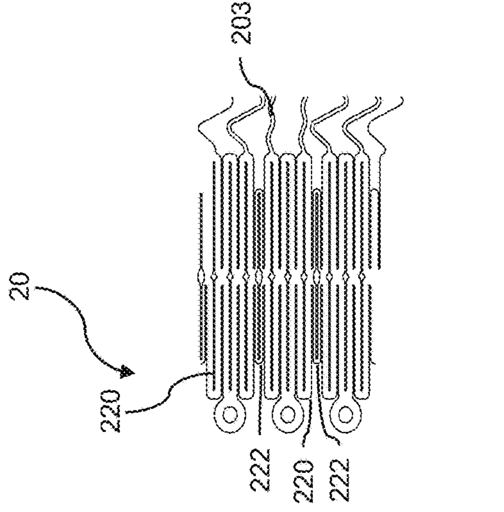

FIGS. 12*a* to 12*c* illustrate another embodiment of a stent 20 useable in the invention. All three figures show the circumference of stent 20 in an unwound view. However, it should be understood that stent 20 is actually annular, and thus the end shown at the top of each of FIGS. 12*a* to 12*c* is connected to the end shown at the bottom of each. The illustrations can also be understood as a cutting pattern for a laser cutting process. FIG. 12*a* shows stent 20 in the crimped state with minimum diameter Dmin. FIG. 12*b* then shows stent 20 at nominal diameter DN, and FIG. 12*c* at maximum diameter Dmax, i.e., in the fully expanded state.

As in the first embodiment of stent 20 of FIG. 7, stent 20 according to FIGS. 12*a* to 12*c* has three first circumferential segments 220 and three second circumferential segments 222. The second circumferential segments 222 each have two second struts 204*a* per ring segment 202, 202*a*, which are connected to each other via a second peak or crown 207*a*. The first circumferential segments 220 have six first struts 204 per ring segment 202, 202*a*. The six first struts 204 form three first prongs 24 in each first circumferential segment 220 (see FIG. 12*b*), of which the middle prong is optionally provided with an anchorage 25, here formed as a ring. The second struts 204*a* each jointly form a second prong 226. The first width b1 of the first struts 204 is again significantly larger than the second width b2 of the second struts 204*a*, here by a factor of about 3.

In contrast to the first embodiment of FIG. 7, the second struts 204*a* of the second circumference segments 222 have a different length than the first struts 204 of the first circumference segments 220. Specifically, the second struts 204*a* have a second length L2, while the first struts 204 have a first length L1. In this embodiment example (FIGS. 12*a* to 12*c*), the second length L2 is shorter than the first length L1. This may slightly increase the stiffness but limit the maximum diameter Dmax, which may also be beneficial to prevent excessive remodeling.

The first struts 204 of the adjacent ring segments 202, 202*a* are each arranged in opposite directions so that they form first cells 240. Similarly, the second struts 204*a* of the adjacent ring segments 202, 202*a* form second cells 242. Since the second struts 204*a* are shorter here than the first struts 204, the second cells 242 are smaller than the first cells 240, in this case by about ⅓.

Figures 13A, 13B, 13C:
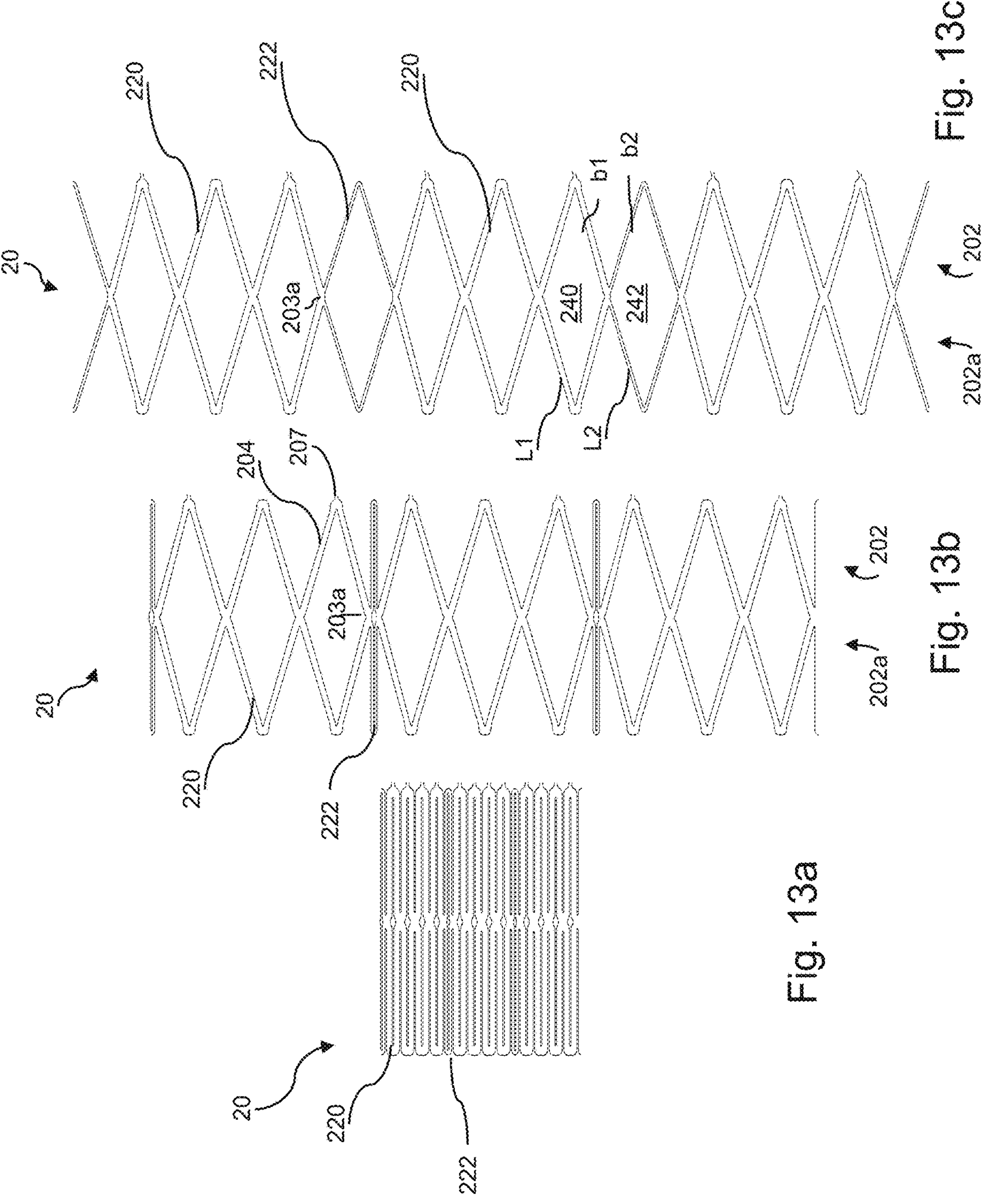
FIGS. 13*a* to 13*c* show an annular segment of the stent in another embodiment in a crimped state, at nominal diameter and at maximum diameter.

FIGS. 13*a* to 13*c* illustrate in the same manner as FIGS. 12*a* to 12*c* the stent 20 in a further embodiment. Identical and similar elements are designated with the same reference signs as in FIGS. 12*a* to 12*c*, and the following essentially the differences to the embodiment of FIGS. 12*a* to 12*c* is described.

In the example shown in FIGS. 13*a* to 13*c*, all struts, the first struts 204 and the second struts 204*a*, have the same length, in this case L1. The different stiffnesses and thus also radial forces are represented in this embodiment exclusively via the width of the respective struts. The first struts 204 have a first width b1 and the second struts 204*a* have a second width b2. Since all struts have the same length, the first and second cells 240, 242 formed by the struts are also essentially identical.

Figures 14A, 14B, 14C:
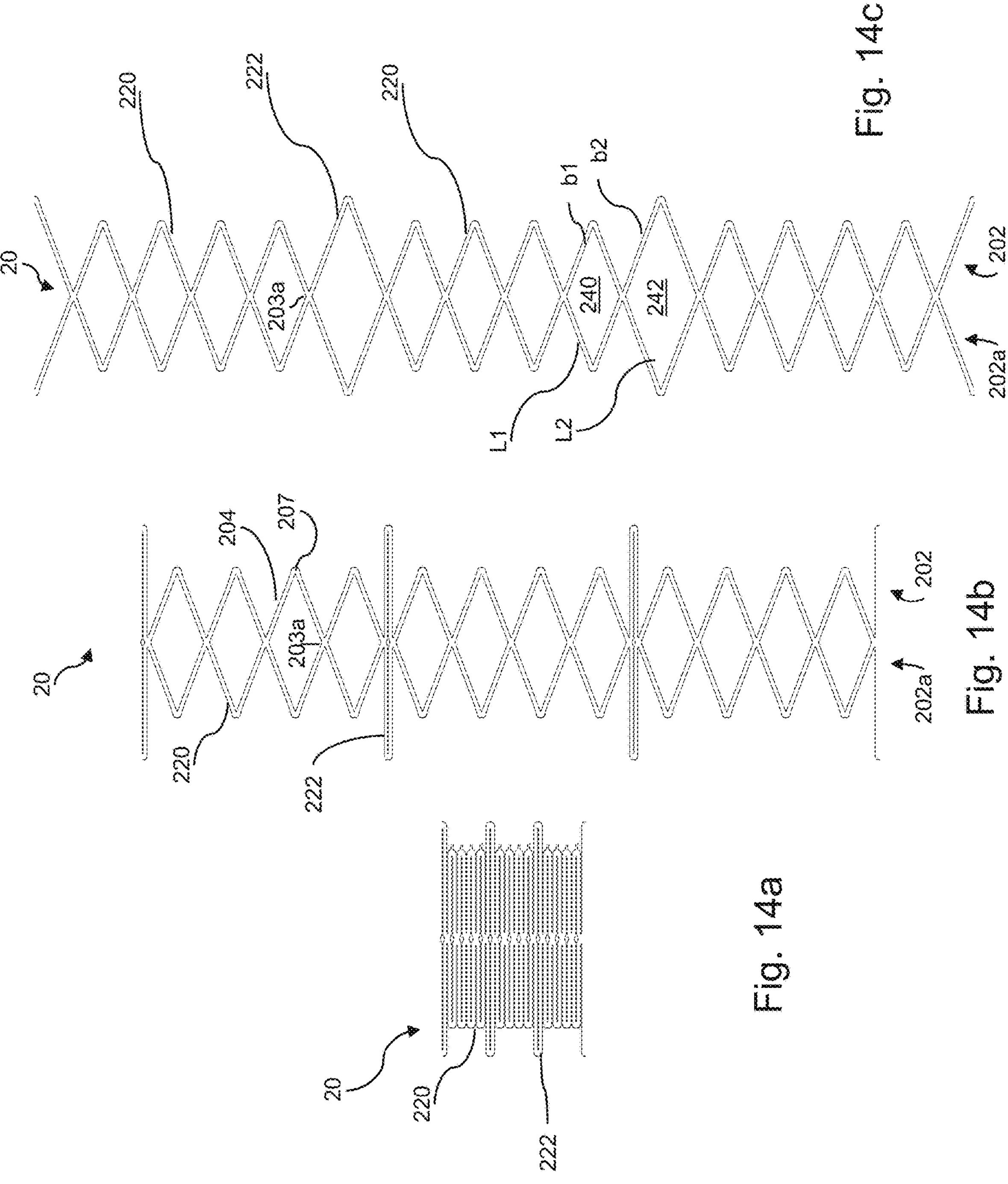
FIGS. 14*a* to 14*c* show an annular segment of the stent in another embodiment in a crimped state, at nominal diameter and at maximum diameter.

FIGS. 14*a* to 14*c* illustrate in the same manner as FIGS. 12*a* to 12*c* the stent 20 in a further embodiment. Identical and similar elements are designated with the same reference signs as in FIGS. 12*a* to 12*c*, and the following essentially the differences to the embodiment of FIGS. 12*a* to 12*c* is described.

In contrast to the embodiment of FIGS. 12*a* to 12*c*, all struts, the first struts 204 and the second struts 204*a* in the embodiment of FIGS. 14*a* to 14*c* have the same struts width, here b1. In this embodiment, the different stiffness or, respectively, the associated radial force is represented exclusively by the length of the struts. While the first struts 204 have a length L1, the second struts 204*a* have an increased length L2. Due to the thus shortened lever acting on the peaks or crowns 203, 203*a*, the stiffness of the second circumferential segments 222 is reduced. A ratio L2/L1 is about 3/2 in this embodiment, but can also be chosen larger or smaller, depending on the application. This in turn also results in different cell sizes of the first and second cells 240, 242. In this respect, this embodiment can also be described in such a way that the second circumference segments 222 form larger cells than the first circumference segments 220.

Another difference compared to the embodiments of FIGS. 12*a* to 12*c* and 13*a* to 13*c* is that the first circumferential segments 220 each have four pairs of first struts 204 and thus also four first cells 240, whereas in the embodiment of FIGS. 12*a* to 12*c* and 13*a* to 13*c* only three first cells 240 are provided in each case.

Figure 15:
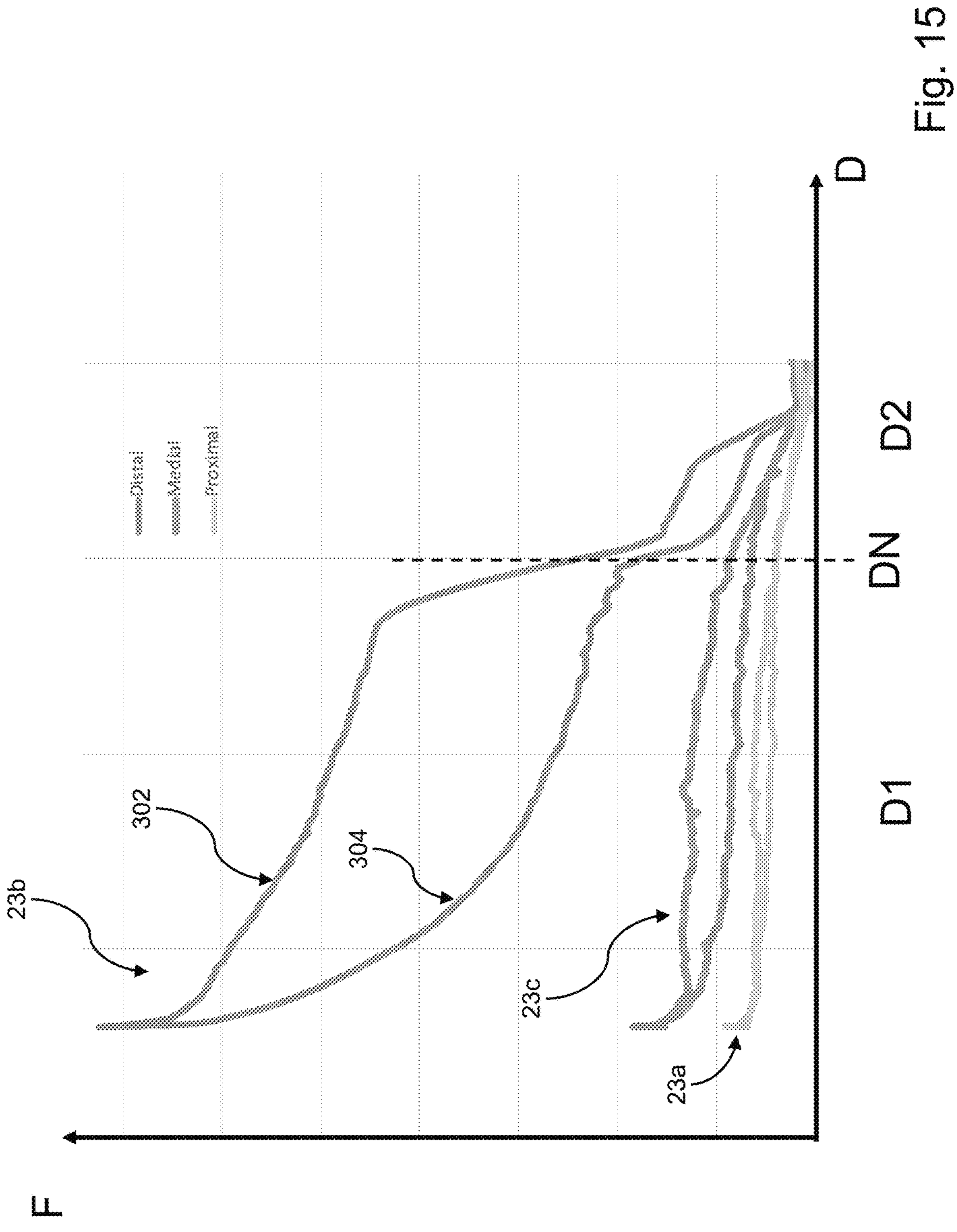
FIG. 15 shows a diagram similar to FIGS. 10 and 11 illustrating the relationship between radial force and expansion/diameter of a stent.

FIG. 15 now illustrated a force-diameter profile of a stent 20 with three sections, a proximal section 23*a*, a medial section 23*c* and a distal section 23*b*. The different sections are in accordance with stent 20 shown in FIG. 5 above. Different than in FIGS. 10 and 11, for each section not only the force-diameter-profile for expanding the stent (lower curve for each section) but also the force-diameter-profile for compressing the stent (upper curve for each section) is shown. Again, similar to FIGS. 10 and 11 also the nominal diameter DN, as well as the first diameter range D1 and the second diameter range D2 are indicated and it will be understood that also other features which already have been described with respect to FIGS. 10 and 11 can be found in FIG. 15, too. The upper curve 302 (only indicated for the distal section 23*b*) describes the so-called radial-resistive force (RRF), i.e., the force the stent 20 is exerting when being compressed from an expanded state to a crimped state. The lower curve 304 (again, only indicated for the distal section 23*b*) describes the so-called chronic outward force (COF), i.e., the force the stent 20 is permanently exerting on its surrounding vessel wall. In FIG. 15 it is apparent, that for a given diameter of either compression or expansion, the exerted force (radial force) of the distal section 23*b* is highest and there may be a factor of about 9 to the proximal section 23*a* and a factor of about 4 to the medial section 23*c*.

The invention claimed is:

1. A planning method for defining a placement position of a stent in an abdominal aorta of a subject, the method comprising:
- providing image data representing at least a portion of the abdominal aorta of the subject;
- identifying, in said image data:
  - an abdominal aortic aneurysm portion of the abdominal aorta having an aneurysm sac and an aneurysm neck,
  - a distal end of the aneurysm neck,
  - a lower renal aortic ostium,
  - a first distance between a distal end of the lower renal aortic ostium and the distal end of the aneurysm neck, and
  - a second distance between a proximal end of the lower renal aortic ostium and the distal end of the aneurysm neck;
- comparing the first distance with a minimum stent length;
- selecting a stent length smaller than the first distance or larger than the second distance if the first distance is larger than the minimum stent length;
- selecting the stent length larger than the second distance if the first distance is smaller than the minimum stent length; and
- defining a stent placement position based on the selected stent length such that a distal end of the stent is aligned with the distal end of the aneurysm neck.

2. The planning method of claim 1, wherein the stent placement position is defined such that a proximal end of the stent is positioned between the distal end of the aneurysm neck and the distal end of the lower renal aortic ostium or proximal of the proximal end of the lower renal aortic ostium.

3. The planning method of claim 1, wherein the identifying, in said image data, further comprises:
- a higher renal aortic ostium; and
- a third distance between a distal end of the higher renal aortic ostium and the distal end of the aneurysm neck, and
- a fourth distance between a proximal end of the higher renal aortic ostium and the distal end of the aneurysm neck.

4. The planning method of claim 3, further comprising:
- comparing the third distance with the minimum stent length; and
- selecting the stent length smaller than the third distance or larger than the fourth distance if the third distance is larger than the minimum stent length; and
- selecting the stent length larger than the fourth distance if the third distance is smaller than the minimum stent length.

5. The planning method of claim 1, wherein identifying, in said image data, further comprises:
- a superior mesenteric aortic ostium,
- a fifth distance between a distal end of the superior mesenteric aortic ostium and the distal end of the aneurysm neck, and a sixth distance between a proximal end of the superior mesenteric aortic ostium and the distal end of the aneurysm neck.

6. The planning method of claim 5, further comprising:

comparing the fifth distance with the minimum stent length; and selecting the stent length smaller than the fifth distance if the fifth distance is larger than the minimum stent length.

7. The planning method of claim 1, wherein identifying, in said image data, further comprises a neck diameter at the distal end of the aneurysm neck, the planning method further comprising:

selecting a nominal stent diameter based on the neck diameter.

8. The planning method of claim 7, wherein the nominal stent diameter is between 1.05 and 1.25 times the neck diameter.

9. The planning method of claim 1, wherein identifying, in said image data, further comprises an aorta diameter at a position proximal of the proximal end of the lower renal aortic ostium, the planning method further comprising:

selecting a nominal stent diameter based on the aorta diameter.

10. The planning method of claim 1, wherein the minimum stent length is between 20 mm and 35 mm.

11. The planning method of claim 1, further comprising:

generating pre-surgical image data based on said image data and including stent placement data representing said placement position of the stent, wherein said pre-surgical image data includes at least one landmark of the subject.

12. The planning method of claim 11, wherein the stent placement data is defined relative to said landmark of the subject.

13. The planning method of claim 1, wherein said stent has a proximal section and a distal section, and wherein the placement position is defined such that said distal section is positioned adjacent the aneurysm sac and said proximal section is positioned away from the aneurysm sac.

14. The planning method of claim 13, wherein a radial force of said distal section is higher than a radial force of said proximal section.

15. The planning method of claim 14, wherein a ratio of the radial force of the distal section to the radial force of the proximal section is between 1.1 and 10.0.

16. The planning method of claim 1, wherein the stent has a crimped state with a minimum diameter and an expanded state with a nominal diameter, wherein the stent has a first expansion characteristic for a first diameter range smaller than the nominal diameter, and wherein the stent has a second expansion characteristic for a second diameter range larger than the nominal diameter.

17. The planning method of claim 16, wherein the first expansion characteristic is a first chronic outward force, the second expansion characteristic is a second chronic outward force that is lower than the first chronic outward force.

18. A method comprising placing a stent in an abdominal aorta of a subject at a placement position defined by the planning method of claim 1.

19. A method comprising:

determining, based on image data of a subject, a first distance between a distal end of a lower renal aortic ostium and a distal end of an aneurysm neck;

determining, based on the image data of the subject, a second distance between a proximal end of the lower renal aortic ostium and the distal end of the aneurysm neck;

comparing the first distance with a minimum stent length;

selecting a stent length smaller than the first distance or larger than the second distance if the first distance is larger than the minimum stent length;

selecting the stent length larger than the second distance if the first distance is smaller than the minimum stent length; and defining a stent placement position based on the selected stent length such that a distal end of a stent is aligned with the distal end of the aneurysm neck.

20. The method of claim 19, further comprising placing the stent in the abdominal aorta of the subject at the stent placement position.

21. A method comprising placing a stent in an abdominal aorta of a subject at a placement position defined by the method of claim 19.

22. An imaging apparatus for displaying a placement position of a stent in an abdominal aorta of a subject, the imaging apparatus comprising:

a representation providing unit for providing image data representing at least a portion of the abdominal aorta of the subject;

an identification unit for identifying, in said image data:

an abdominal aortic aneurysm portion of the abdominal aorta having an aneurysm sac and an aneurysm neck, a distal end of the aneurysm neck, a lower renal aortic ostium, a first distance between a distal end of the lower renal aortic ostium and the distal end of the aneurysm neck, and a second distance between a proximal end of the lower renal aortic ostium and the distal end of the aneurysm neck;

a placement position providing unit for:

comparing the first distance with a minimum stent length;

selecting a stent length smaller than the first distance or larger than the second distance if the first distance is larger than the minimum stent length;

selecting the stent length larger than the second distance if the first distance is smaller than the minimum stent length; and defining a stent placement position based on the selected stent length such that a distal end of the stent is aligned with the distal end of the aneurysm neck; and a display for displaying the stent placement position.

* * * * *